US012562004B2

(12) United States Patent
Jarvenpaa

(10) Patent No.: US 12,562,004 B2
(45) Date of Patent: *Feb. 24, 2026

(54) APPARATUS FOR A NEAR-EYE DISPLAY

(71) Applicant: Magic Leap, Inc., Plantation, FL (US)

(72) Inventor: Toni Jarvenpaa, Akaa (FI)

(73) Assignee: Magic Leap, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/348,732

(22) Filed: Jul. 7, 2023

(65) Prior Publication Data

US 2023/0351808 A1      Nov. 2, 2023

Related U.S. Application Data

(63) Continuation of application No. 17/713,505, filed on Apr. 5, 2022, now Pat. No. 11,756,335, which is a
(Continued)

(30) Foreign Application Priority Data

Feb. 26, 2015    (EP) ..................................... 15156666

(51) Int. Cl.
G06K 9/00          (2022.01)
A61B 3/113          (2006.01)
(Continued)

(52) U.S. Cl.
CPC .............. G06V 40/19 (2022.01); A61B 3/113 (2013.01); G02B 5/208 (2013.01); G02B 6/0016 (2013.01);
(Continued)

(58) Field of Classification Search
None
See application file for complete search history.

(56) References Cited

U.S. PATENT DOCUMENTS 4,344,092 A      8/1982    Miller
4,652,930 A      3/1987    Crawford
(Continued)

FOREIGN PATENT DOCUMENTS

CN          100416340 C      9/2008
CN          101449270 A      6/2009
(Continued)

OTHER PUBLICATIONS

"ARToolKit: Hardware", https://web.archive.org/web/20051013062315/http://www.hitl.washington.edu:80/artoolkit/documentation/hardware.htm (downloaded Oct. 26, 2020), Oct. 13, 2015, (3 pages).
(Continued)

*Primary Examiner* — Lindsay J Uhl
(74) *Attorney, Agent, or Firm* — Stephen M. De Klerk

(57)          ABSTRACT

An apparatus for providing gaze tracking in a near-eye display. Certain examples provide an apparatus including a light modulator configured to receive light of a first range of wavelengths and generate an image beam therefrom. The light modulator is further configured to receive light of a second range of wavelengths and generate a probe beam therefrom. The apparatus also includes one or more light guides including one or more in-coupling element areas, and one or more out-coupling element areas. The one or more in-coupling diffractive element areas are configured to receive and in-couple the image beam and the probe beam into the one or more light guides. The one or more out-coupling element areas are configured to out-couple, from the one or more light guides: the image beam to a user's eye for user viewing, and the probe beam to the user's eye for detection of reflection therefrom.

10 Claims, 5 Drawing Sheets

Related U.S. Application Data continuation of application No. 17/105,848, filed on Nov. 27, 2020, now Pat. No. 11,347,960, which is a continuation of application No. 15/552,897, filed as application No. PCT/FI2016/050072 on Feb. 5, 2016, now Pat. No. 10,878,235.

(51) Int. Cl.

| | |
|---|---|
| *F21V 8/00* | (2006.01) |
| *G02B 5/20* | (2006.01) |
| *G02B 27/00* | (2006.01) |
| *G02B 27/01* | (2006.01) |
| *G02B 27/42* | (2006.01) |
| *G06V 40/19* | (2022.01) |
| *H04N 5/225* | (2006.01) |
| *H04N 5/235* | (2006.01) |
| *H04N 5/33* | (2023.01) |
| *H04N 23/11* | (2023.01) |
| *H04N 23/56* | (2023.01) |
| *H04N 23/74* | (2023.01) |

(52) U.S. Cl.
CPC ....... *G02B 6/0036* (2013.01); *G02B 27/0093* (2013.01); *G02B 27/0172* (2013.01); *H04N 23/11* (2023.01); *H04N 23/56* (2023.01); *H04N 23/74* (2023.01); *G02B 2027/0112* (2013.01); *G02B 2027/0123* (2013.01); *G02B 2027/0125* (2013.01); *G02B 2027/0132* (2013.01); *G02B 2027/0138* (2013.01); *G02B 2027/0178* (2013.01); *G02B 27/4205* (2013.01); *G06V 2201/07* (2022.01)

(56) References Cited

U.S. PATENT DOCUMENTS

| | | | |
|---|---|---|---|
| 4,810,080 A | 3/1989 | Grendol et al. | |
| 4,997,268 A | 3/1991 | Dauvergne | |
| 5,007,727 A | 4/1991 | Kahaney et al. | |
| 5,074,295 A | 12/1991 | Willis | |
| 5,240,220 A | 8/1993 | Elberbaum | |
| 5,251,635 A | 10/1993 | Dumoulin et al. | |
| 5,410,763 A | 5/1995 | Bolle | |
| 5,455,625 A | 10/1995 | Englander | |
| 5,495,286 A | 2/1996 | Adair | |
| 5,497,463 A | 3/1996 | Stein et al. | |
| 5,659,701 A | 8/1997 | Amit et al. | |
| 5,682,255 A | 10/1997 | Friesem et al. | |
| 5,689,669 A | 11/1997 | Lynch | |
| 5,826,092 A | 10/1998 | Flannery | |
| 5,854,872 A | 12/1998 | Tai | |
| 5,864,365 A | 1/1999 | Sramek et al. | |
| 5,937,202 A | 8/1999 | Crosetto | |
| 6,002,853 A | 12/1999 | de Hond | |
| 6,012,811 A | 1/2000 | Chao et al. | |
| 6,016,160 A | 1/2000 | Coombs et al. | |
| 6,064,749 A | 5/2000 | Hirota et al. | |
| 6,076,927 A | 6/2000 | Owens | |
| 6,079,982 A | 6/2000 | Meader | |
| 6,117,923 A | 9/2000 | Amagai et al. | |
| 6,119,147 A | 9/2000 | Toomey et al. | |
| 6,124,977 A | 9/2000 | Takahashi | |
| 6,179,619 B1 | 1/2001 | Tanaka | |
| 6,191,809 B1 | 2/2001 | Hori et al. | |
| 6,219,045 B1 | 4/2001 | Leahy et al. | |
| 6,243,091 B1 | 6/2001 | Berstis | |
| 6,271,843 B1 | 8/2001 | Lection et al. | |
| 6,362,817 B1 | 3/2002 | Powers et al. | |
| 6,375,369 B1 | 4/2002 | Schneider et al. | |
| 6,385,735 B1 | 5/2002 | Wilson | |
| 6,396,522 B1 | 5/2002 | Vu | |
| 6,414,679 B1 | 7/2002 | Miodonski et al. | |
| 6,538,655 B1 | 3/2003 | Kubota | |
| 6,541,736 B1 | 4/2003 | Huang et al. | |
| 6,570,563 B1 | 5/2003 | Honda | |
| 6,573,903 B2 | 6/2003 | Gantt | |
| 6,590,593 B1 | 7/2003 | Robertson et al. | |
| 6,621,508 B1 | 9/2003 | Shiraishi et al. | |
| 6,690,393 B2 | 2/2004 | Heron et al. | |
| 6,757,068 B2 | 6/2004 | Foxlin | |
| 6,784,901 B1 | 8/2004 | Harvey et al. | |
| 6,961,055 B2 | 11/2005 | Doak | |
| 7,046,515 B1 | 5/2006 | Wyatt | |
| 7,051,219 B2 | 5/2006 | Hwang | |
| 7,076,674 B2 | 7/2006 | Cervantes | |
| 7,111,290 B1 | 9/2006 | Yates, Jr | |
| 7,119,819 B1 | 10/2006 | Robertson et al. | |
| 7,211,986 B1 | 5/2007 | Flowerdew et al. | |
| 7,219,245 B1 | 5/2007 | Raghuvanshi | |
| 7,382,288 B1 | 6/2008 | Wilson | |
| 7,414,629 B2 | 8/2008 | Santodomingo | |
| 7,431,453 B2 | 10/2008 | Hogan | |
| 7,467,356 B2 | 12/2008 | Gettman et al. | |
| 7,542,040 B2 | 6/2009 | Templeman | |
| 7,573,640 B2 | 8/2009 | Nivon et al. | |
| 7,653,877 B2 | 1/2010 | Matsuda | |
| 7,663,625 B2 | 2/2010 | Chartier et al. | |
| 7,724,980 B1 | 5/2010 | Shenzhi | |
| 7,746,343 B1 | 6/2010 | Charaniya et al. | |
| 7,751,662 B2 | 7/2010 | Kleemann | |
| 7,758,185 B2 | 7/2010 | Lewis | |
| 7,788,323 B2 | 8/2010 | Greenstein et al. | |
| 7,804,507 B2 | 9/2010 | Yang et al. | |
| 7,814,429 B2 | 10/2010 | Buffet et al. | |
| 7,817,150 B2 | 10/2010 | Reichard et al. | |
| 7,844,724 B2 | 11/2010 | Van Wie et al. | |
| 8,060,759 B1 | 11/2011 | Arnan et al. | |
| 8,120,851 B2 | 2/2012 | Iwasa | |
| 8,214,660 B2 | 7/2012 | Capps, Jr. | |
| 8,246,408 B2 | 8/2012 | Elliot | |
| 8,353,594 B2 | 1/2013 | Lewis | |
| 8,360,578 B2 * | 1/2013 | Nummela ............... A61B 3/113 351/221 |
| 8,508,676 B2 | 8/2013 | Silverstein et al. | |
| 8,547,638 B2 | 10/2013 | Levola | |
| 8,605,764 B1 | 12/2013 | Rothaar et al. | |
| 8,619,365 B2 | 12/2013 | Harris et al. | |
| 8,696,113 B2 | 4/2014 | Lewis | |
| 8,698,701 B2 | 4/2014 | Margulis | |
| 8,733,927 B1 | 5/2014 | Lewis | |
| 8,736,636 B2 | 5/2014 | Kang | |
| 8,759,929 B2 | 6/2014 | Shiozawa et al. | |
| 8,793,770 B2 | 7/2014 | Lim | |
| 8,823,855 B2 | 9/2014 | Hwang | |
| 8,847,988 B2 | 9/2014 | Geisner et al. | |
| 8,874,673 B2 | 10/2014 | Kim | |
| 9,010,929 B2 | 4/2015 | Lewis | |
| 9,015,501 B2 | 4/2015 | Gee | |
| 9,086,537 B2 | 7/2015 | Iwasa et al. | |
| 9,095,437 B2 | 8/2015 | Boyden et al. | |
| 9,239,473 B2 | 1/2016 | Lewis | |
| 9,244,293 B2 | 1/2016 | Lewis | |
| 9,244,533 B2 | 1/2016 | Friend et al. | |
| 9,285,872 B1 | 3/2016 | Raffle et al. | |
| 9,383,823 B2 | 7/2016 | Geisner et al. | |
| 9,489,027 B1 | 11/2016 | Ogletree | |
| 9,519,305 B2 | 12/2016 | Wolfe | |
| 9,581,820 B2 | 2/2017 | Robbins | |
| 9,582,060 B2 | 2/2017 | Balatsos | |
| 9,658,473 B2 | 5/2017 | Lewis | |
| 9,671,566 B2 | 6/2017 | Abovitz et al. | |
| 9,671,615 B1 | 6/2017 | Vallius et al. | |
| 9,696,795 B2 | 7/2017 | Marcolina et al. | |
| 9,798,144 B2 | 10/2017 | Sako et al. | |
| 9,874,664 B2 | 1/2018 | Stevens et al. | |
| 9,880,441 B1 | 1/2018 | Osterhout | |
| 9,918,058 B2 | 3/2018 | Takahasi et al. | |
| 9,955,862 B2 | 5/2018 | Freeman et al. | |
| 9,978,118 B1 | 5/2018 | Ozgumer et al. | |
| 9,996,797 B1 | 6/2018 | Holz et al. | |
| 10,018,844 B2 | 7/2018 | Levola et al. | |
| 10,082,865 B1 | 9/2018 | Raynal et al. | |

(56) References Cited

U.S. PATENT DOCUMENTS

| | | | |
|---|---|---|---|
| 10,151,937 B2 | 12/2018 | Lewis | |
| 10,185,147 B2 | 1/2019 | Lewis | |
| 10,218,679 B1 | 2/2019 | Jawahar | |
| 10,241,545 B1 | 3/2019 | Richards et al. | |
| 10,317,680 B1 | 6/2019 | Richards et al. | |
| 10,436,594 B2 | 10/2019 | Belt et al. | |
| 10,516,853 B1 | 12/2019 | Gibson et al. | |
| 10,527,853 B2 | 1/2020 | Kimmel | |
| 10,551,879 B1 | 2/2020 | Richards et al. | |
| 10,578,870 B2 | 3/2020 | Kimmel | |
| 10,646,283 B2 | 5/2020 | Johnson et al. | |
| 10,698,202 B2 | 6/2020 | Kimmel et al. | |
| 10,825,424 B2 | 11/2020 | Zhang | |
| 10,856,107 B2 | 12/2020 | Mycek et al. | |
| 10,987,176 B2 | 4/2021 | Poltaretskyi et al. | |
| 11,190,681 B1 | 11/2021 | Brook et al. | |
| 11,199,713 B2 | 12/2021 | Kimmel | |
| 11,209,656 B1 | 12/2021 | Choi et al. | |
| 11,236,993 B1 | 2/2022 | Hall et al. | |
| 11,262,585 B2 | 3/2022 | Potnis et al. | |
| 11,874,468 B2 | 1/2024 | Kimmel | |
| 11,900,626 B2 | 2/2024 | Tang | |
| 2001/0010598 A1 | 8/2001 | Aritake et al. | |
| 2001/0018667 A1 | 8/2001 | Kim | |
| 2002/0007463 A1 | 1/2002 | Fung | |
| 2002/0063913 A1 | 5/2002 | Nakamura et al. | |
| 2002/0071050 A1 | 6/2002 | Homberg | |
| 2002/0095463 A1 | 7/2002 | Matsuda | |
| 2002/0108064 A1 | 8/2002 | Nunally | |
| 2002/0113820 A1 | 8/2002 | Robinson et al. | |
| 2002/0122648 A1 | 9/2002 | Mule' et al. | |
| 2002/0140848 A1 | 10/2002 | Cooper et al. | |
| 2003/0028816 A1 | 2/2003 | Bacon | |
| 2003/0048456 A1 | 3/2003 | Hill | |
| 2003/0067685 A1 | 4/2003 | Niv | |
| 2003/0077458 A1 | 4/2003 | Korenaga et al. | |
| 2003/0080976 A1 | 5/2003 | Satoh et al. | |
| 2003/0115494 A1 | 6/2003 | Cervantes | |
| 2003/0218614 A1 | 11/2003 | Lavelle et al. | |
| 2003/0219992 A1 | 11/2003 | Schaper | |
| 2003/0226047 A1 | 12/2003 | Park | |
| 2004/0001533 A1 | 1/2004 | Tran et al. | |
| 2004/0021600 A1 | 2/2004 | Wittenberg | |
| 2004/0025069 A1 | 2/2004 | Gary et al. | |
| 2004/0042377 A1 | 3/2004 | Nikoloai et al. | |
| 2004/0073822 A1 | 4/2004 | Greco | |
| 2004/0073825 A1 | 4/2004 | Itoh | |
| 2004/0111248 A1 | 6/2004 | Granny et al. | |
| 2004/0113887 A1 | 6/2004 | Pair et al. | |
| 2004/0174496 A1 | 9/2004 | Ji et al. | |
| 2004/0186902 A1 | 9/2004 | Stewart | |
| 2004/0193441 A1 | 9/2004 | Altieri | |
| 2004/0201857 A1 | 10/2004 | Foxlin | |
| 2004/0238732 A1 | 12/2004 | State et al. | |
| 2004/0240072 A1 | 12/2004 | Schindler et al. | |
| 2004/0246391 A1 | 12/2004 | Travis | |
| 2004/0268159 A1 | 12/2004 | Aasheim et al. | |
| 2005/0001977 A1 | 1/2005 | Zelman | |
| 2005/0034002 A1 | 2/2005 | Flautner | |
| 2005/0093719 A1 | 5/2005 | Okamoto et al. | |
| 2005/0128212 A1 | 6/2005 | Edecker et al. | |
| 2005/0157159 A1 | 7/2005 | Komiya et al. | |
| 2005/0177385 A1 | 8/2005 | Hul | |
| 2005/0231599 A1 | 10/2005 | Yamasaki | |
| 2005/0273792 A1 | 12/2005 | Inohara et al. | |
| 2006/0013435 A1 | 1/2006 | Rhoads | |
| 2006/0015821 A1 | 1/2006 | Jacques Parker et al. | |
| 2006/0019723 A1 | 1/2006 | Vorenkamp | |
| 2006/0038880 A1 | 2/2006 | Starkweather et al. | |
| 2006/0050224 A1 | 3/2006 | Smith | |
| 2006/0090092 A1 | 4/2006 | Verhulst | |
| 2006/0126181 A1 | 6/2006 | Levola | |
| 2006/0126182 A1 | 6/2006 | Levola | |
| 2006/0129852 A1 | 6/2006 | Bonola | |
| 2006/0132914 A1 | 6/2006 | Weiss et al. | |
| 2006/0179329 A1 | 8/2006 | Terechko | |
| 2006/0221448 A1 | 10/2006 | Nivon et al. | |
| 2006/0228073 A1 | 10/2006 | Mukawa et al. | |
| 2006/0250322 A1 | 11/2006 | Hall et al. | |
| 2006/0259621 A1 | 11/2006 | Ranganathan | |
| 2006/0268220 A1 | 11/2006 | Hogan | |
| 2007/0058248 A1 | 3/2007 | Nguyen et al. | |
| 2007/0103836 A1 | 5/2007 | Oh | |
| 2007/0124730 A1 | 5/2007 | Pytel | |
| 2007/0159673 A1 | 7/2007 | Freeman et al. | |
| 2007/0185398 A1 | 8/2007 | Kimura et al. | |
| 2007/0188837 A1 | 8/2007 | Shimizu et al. | |
| 2007/0198886 A1 | 8/2007 | Saito | |
| 2007/0204672 A1 | 9/2007 | Huang et al. | |
| 2007/0213952 A1 | 9/2007 | Cirelli | |
| 2007/0283247 A1 | 12/2007 | Brenneman et al. | |
| 2008/0002259 A1 | 1/2008 | Ishizawa et al. | |
| 2008/0002260 A1 | 1/2008 | Arrouy et al. | |
| 2008/0030429 A1 | 2/2008 | Hailpern | |
| 2008/0043334 A1 | 2/2008 | Itzkovitch et al. | |
| 2008/0046773 A1 | 2/2008 | Ham | |
| 2008/0050013 A1 | 2/2008 | Munro | |
| 2008/0063802 A1 | 3/2008 | Maula et al. | |
| 2008/0068557 A1 | 3/2008 | Menduni et al. | |
| 2008/0082480 A1 | 4/2008 | Gounares et al. | |
| 2008/0125218 A1 | 5/2008 | Collins | |
| 2008/0146942 A1 | 6/2008 | Dala-Krishna | |
| 2008/0173036 A1 | 7/2008 | Willaims | |
| 2008/0177506 A1 | 7/2008 | Kim | |
| 2008/0183190 A1 | 7/2008 | Adcox et al. | |
| 2008/0205838 A1 | 8/2008 | Crippa et al. | |
| 2008/0215907 A1 | 9/2008 | Wilson | |
| 2008/0225393 A1 | 9/2008 | Rinko | |
| 2008/0235570 A1 | 9/2008 | Sawada et al. | |
| 2008/0246693 A1 | 10/2008 | Hailpern et al. | |
| 2008/0316768 A1 | 12/2008 | Travis | |
| 2009/0076791 A1 | 3/2009 | Rhoades et al. | |
| 2009/0091583 A1 | 4/2009 | McCoy | |
| 2009/0153797 A1 | 6/2009 | Allon et al. | |
| 2009/0177445 A1 | 7/2009 | Capps, Jr. et al. | |
| 2009/0224416 A1 | 9/2009 | Laakkonen et al. | |
| 2009/0245730 A1 | 10/2009 | Kleemann | |
| 2009/0287728 A1 | 11/2009 | Martine et al. | |
| 2009/0300528 A1 | 12/2009 | Stambaugh | |
| 2009/0310633 A1 | 12/2009 | Ikegami | |
| 2010/0005326 A1 | 1/2010 | Archer | |
| 2010/0019962 A1 | 1/2010 | Fujita | |
| 2010/0056274 A1 | 3/2010 | Uusitalo et al. | |
| 2010/0060970 A1 | 3/2010 | Harris et al. | |
| 2010/0063854 A1 | 3/2010 | Purvis et al. | |
| 2010/0070378 A1 | 3/2010 | Trotman et al. | |
| 2010/0079841 A1 | 4/2010 | Levola | |
| 2010/0115428 A1 | 5/2010 | Shuping et al. | |
| 2010/0153934 A1 | 6/2010 | Lachner | |
| 2010/0194632 A1 | 8/2010 | Raento et al. | |
| 2010/0205541 A1 | 8/2010 | Rappaport et al. | |
| 2010/0214284 A1 | 8/2010 | Rieffel et al. | |
| 2010/0232016 A1 | 9/2010 | Landa et al. | |
| 2010/0232031 A1 | 9/2010 | Batchko et al. | |
| 2010/0244168 A1 | 9/2010 | Shiozawa et al. | |
| 2010/0274567 A1 | 10/2010 | Carlson et al. | |
| 2010/0274627 A1 | 10/2010 | Carlson | |
| 2010/0277803 A1 | 11/2010 | Pockett et al. | |
| 2010/0284085 A1 | 11/2010 | Laakkonen | |
| 2010/0287485 A1 | 11/2010 | Bertolami et al. | |
| 2010/0296163 A1 | 11/2010 | Sarikko | |
| 2010/0306715 A1 | 12/2010 | Geisner et al. | |
| 2010/0309687 A1 | 12/2010 | Sampsell et al. | |
| 2010/0321781 A1 | 12/2010 | Levola | |
| 2011/0010636 A1 | 1/2011 | Hamilton, II et al. | |
| 2011/0021263 A1 | 1/2011 | Anderson et al. | |
| 2011/0022870 A1 | 1/2011 | Mcgrane | |
| 2011/0041083 A1 | 2/2011 | Gabai et al. | |
| 2011/0050640 A1 | 3/2011 | Lundback et al. | |
| 2011/0050655 A1 | 3/2011 | Mukawa | |
| 2011/0064268 A1 | 3/2011 | Cobb et al. | |
| 2011/0122240 A1 | 5/2011 | Becker | |
| 2011/0145617 A1 | 6/2011 | Thomson et al. | |
| 2011/0170801 A1 | 7/2011 | Lu et al. | |

(56)         References Cited

U.S. PATENT DOCUMENTS

| | | |
|---|---|---|
| 2011/0218733 A1 | 9/2011 | Hamza et al. |
| 2011/0286735 A1 | 11/2011 | Temblay |
| 2011/0291969 A1 | 12/2011 | Rashid et al. |
| 2011/0317233 A1 | 12/2011 | Hayashibe et al. |
| 2012/0011389 A1 | 1/2012 | Driesen |
| 2012/0050535 A1 | 3/2012 | Densham et al. |
| 2012/0075501 A1 | 3/2012 | Oyagi et al. |
| 2012/0079466 A1 | 3/2012 | Gonion |
| 2012/0081392 A1 | 4/2012 | Arthur |
| 2012/0089854 A1 | 4/2012 | Breakstone |
| 2012/0113235 A1 | 5/2012 | Shintani |
| 2012/0127062 A1 | 5/2012 | Bar-Zeev et al. |
| 2012/0154557 A1 | 6/2012 | Perez et al. |
| 2012/0215094 A1 | 8/2012 | Rahimian et al. |
| 2012/0218301 A1 | 8/2012 | Miller |
| 2012/0246506 A1 | 9/2012 | Knight |
| 2012/0249416 A1 | 10/2012 | Maciocci et al. |
| 2012/0249741 A1 | 10/2012 | Maciocci et al. |
| 2012/0260083 A1 | 10/2012 | Andrews |
| 2012/0280348 A1 | 11/2012 | Chou et al. |
| 2012/0307075 A1 | 12/2012 | Margalit |
| 2012/0307362 A1 | 12/2012 | Silverstein et al. |
| 2012/0314959 A1 | 12/2012 | White et al. |
| 2012/0320460 A1 | 12/2012 | Levola |
| 2012/0326948 A1 | 12/2012 | Crocco et al. |
| 2013/0021486 A1 | 1/2013 | Richardon |
| 2013/0050258 A1 | 2/2013 | Liu et al. |
| 2013/0050642 A1 | 2/2013 | Lewis et al. |
| 2013/0050833 A1 | 2/2013 | Lewis et al. |
| 2013/0051730 A1 | 2/2013 | Travers et al. |
| 2013/0061240 A1 | 3/2013 | Yan et al. |
| 2013/0077049 A1* | 3/2013 | Bohn .............. G02B 27/0093 351/210 |
| 2013/0077170 A1 | 3/2013 | Ukuda |
| 2013/0094148 A1 | 4/2013 | Sloane |
| 2013/0129282 A1 | 5/2013 | Li |
| 2013/0162940 A1 | 6/2013 | Kurtin et al. |
| 2013/0169923 A1 | 7/2013 | Schnoll et al. |
| 2013/0205126 A1 | 8/2013 | Kruglick |
| 2013/0222386 A1 | 8/2013 | Tannhauser et al. |
| 2013/0268257 A1 | 10/2013 | Hu |
| 2013/0278633 A1 | 10/2013 | Ahn et al. |
| 2013/0308861 A1 | 11/2013 | Cordara |
| 2013/0314789 A1 | 11/2013 | Saarikko et al. |
| 2013/0318276 A1 | 11/2013 | Dalal |
| 2013/0336138 A1 | 12/2013 | Venkatraman et al. |
| 2013/0342564 A1 | 12/2013 | Kinnebrew et al. |
| 2013/0342570 A1 | 12/2013 | Kinnebrew et al. |
| 2013/0342571 A1 | 12/2013 | Kinnebrew et al. |
| 2013/0343408 A1 | 12/2013 | Cook |
| 2014/0002329 A1 | 1/2014 | Nishimaki et al. |
| 2014/0013098 A1 | 1/2014 | Yeung |
| 2014/0016821 A1 | 1/2014 | Arth et al. |
| 2014/0022819 A1 | 1/2014 | Oh et al. |
| 2014/0078023 A1 | 3/2014 | Ikeda et al. |
| 2014/0082526 A1 | 3/2014 | Park et al. |
| 2014/0119598 A1 | 5/2014 | Ramachandran et al. |
| 2014/0123015 A1 | 5/2014 | Sako et al. |
| 2014/0126769 A1 | 5/2014 | Reitmayr et al. |
| 2014/0140653 A1 | 5/2014 | Brown et al. |
| 2014/0149573 A1 | 5/2014 | Tofighbakhsh et al. |
| 2014/0168260 A1 | 6/2014 | O'Brien et al. |
| 2014/0204438 A1* | 7/2014 | Yamada ................... G02B 5/18 362/608 |
| 2014/0244983 A1 | 8/2014 | McDonald et al. |
| 2014/0266987 A1 | 9/2014 | Magyari |
| 2014/0267419 A1 | 9/2014 | Ballard et al. |
| 2014/0274391 A1 | 9/2014 | Stafford |
| 2014/0282105 A1 | 9/2014 | Nordstrom |
| 2014/0292645 A1 | 10/2014 | Tsurumi et al. |
| 2014/0313228 A1 | 10/2014 | Kasahara |
| 2014/0359589 A1 | 12/2014 | Kodsky et al. |
| 2014/0375680 A1 | 12/2014 | Ackerman et al. |
| 2015/0005785 A1 | 1/2015 | Olson |
| 2015/0009099 A1 | 1/2015 | Queen |
| 2015/0077312 A1 | 3/2015 | Wang |
| 2015/0097719 A1 | 4/2015 | Balachandreswaran et al. |
| 2015/0123966 A1 | 5/2015 | Newman |
| 2015/0130790 A1 | 5/2015 | Vazquez, II et al. |
| 2015/0132003 A1 | 5/2015 | Greiner et al. |
| 2015/0132596 A1 | 5/2015 | Yamada et al. |
| 2015/0134995 A1 | 5/2015 | Park et al. |
| 2015/0138248 A1 | 5/2015 | Schrader |
| 2015/0155939 A1 | 6/2015 | Oshima et al. |
| 2015/0168221 A1 | 6/2015 | Mao et al. |
| 2015/0205126 A1 | 7/2015 | Schowengerdt |
| 2015/0235427 A1 | 8/2015 | Nobori et al. |
| 2015/0235431 A1 | 8/2015 | Schowengerdt |
| 2015/0253651 A1 | 9/2015 | Russell et al. |
| 2015/0256484 A1 | 9/2015 | Cameron |
| 2015/0269784 A1 | 9/2015 | Miyawaki et al. |
| 2015/0294483 A1 | 10/2015 | Wells et al. |
| 2015/0301955 A1 | 10/2015 | Yakovenko et al. |
| 2015/0310657 A1 | 10/2015 | Eden |
| 2015/0338915 A1 | 11/2015 | Publicover et al. |
| 2015/0355481 A1 | 12/2015 | Hilkes et al. |
| 2016/0004102 A1 | 1/2016 | Nisper et al. |
| 2016/0015470 A1 | 1/2016 | Border |
| 2016/0027215 A1 | 1/2016 | Burns et al. |
| 2016/0033770 A1 | 2/2016 | Fujimaki et al. |
| 2016/0051217 A1 | 2/2016 | Douglas et al. |
| 2016/0077338 A1 | 3/2016 | Robbins et al. |
| 2016/0085285 A1 | 3/2016 | Mangione-Smith |
| 2016/0085300 A1 | 3/2016 | Robbins et al. |
| 2016/0091720 A1 | 3/2016 | Stafford et al. |
| 2016/0093099 A1 | 3/2016 | Bridges |
| 2016/0093269 A1 | 3/2016 | Buckley et al. |
| 2016/0103326 A1 | 4/2016 | Kimura et al. |
| 2016/0123745 A1 | 5/2016 | Cotier et al. |
| 2016/0139402 A1 | 5/2016 | Lapstun |
| 2016/0139411 A1 | 5/2016 | Kang et al. |
| 2016/0155273 A1 | 6/2016 | Lyren et al. |
| 2016/0163063 A1 | 6/2016 | Ashman |
| 2016/0180596 A1 | 6/2016 | Gonzalez del Rosario |
| 2016/0187654 A1 | 6/2016 | Border et al. |
| 2016/0191887 A1 | 6/2016 | Casas |
| 2016/0202496 A1 | 7/2016 | Billetz et al. |
| 2016/0217624 A1 | 7/2016 | Finn et al. |
| 2016/0266412 A1 | 9/2016 | Yoshida |
| 2016/0267708 A1 | 9/2016 | Nistico et al. |
| 2016/0274733 A1 | 9/2016 | Hasegawa et al. |
| 2016/0277645 A1 | 9/2016 | Bitouk |
| 2016/0287337 A1 | 10/2016 | Aram et al. |
| 2016/0300388 A1 | 10/2016 | Stafford et al. |
| 2016/0321551 A1 | 11/2016 | Priness et al. |
| 2016/0327798 A1 | 11/2016 | Xiao et al. |
| 2016/0334279 A1 | 11/2016 | Mittleman et al. |
| 2016/0357255 A1 | 12/2016 | Lindh et al. |
| 2016/0370404 A1 | 12/2016 | Quadrat et al. |
| 2016/0370510 A1 | 12/2016 | Thomas |
| 2017/0038607 A1 | 2/2017 | Camara |
| 2017/0060225 A1 | 3/2017 | Zha et al. |
| 2017/0061696 A1 | 3/2017 | Li et al. |
| 2017/0064066 A1 | 3/2017 | Das et al. |
| 2017/0068020 A1 | 3/2017 | Batchko et al. |
| 2017/0100664 A1 | 4/2017 | Osterhout et al. |
| 2017/0102544 A1 | 4/2017 | Vallius et al. |
| 2017/0115487 A1 | 4/2017 | Travis |
| 2017/0122725 A1 | 5/2017 | Yeoh et al. |
| 2017/0123526 A1 | 5/2017 | Trail et al. |
| 2017/0127295 A1 | 5/2017 | Black et al. |
| 2017/0131569 A1 | 5/2017 | Aschwanden et al. |
| 2017/0147066 A1 | 5/2017 | Katz et al. |
| 2017/0160518 A1 | 6/2017 | Lanman et al. |
| 2017/0161951 A1 | 6/2017 | Fix et al. |
| 2017/0172409 A1 | 6/2017 | Cavin et al. |
| 2017/0185261 A1 | 6/2017 | Perez et al. |
| 2017/0192239 A1 | 7/2017 | Nakamura et al. |
| 2017/0201709 A1 | 7/2017 | Igarashi et al. |
| 2017/0205903 A1 | 7/2017 | Miller et al. |
| 2017/0206668 A1 | 7/2017 | Poulos et al. |
| 2017/0213388 A1 | 7/2017 | Margolis et al. |
| 2017/0214893 A1 | 7/2017 | Naftali et al. |
| 2017/0214907 A1 | 7/2017 | Lapstun |

(56) References Cited

U.S. PATENT DOCUMENTS

| | | |
|---|---|---|
| 2017/0219841 A1 | 8/2017 | Popovich et al. |
| 2017/0232345 A1 | 8/2017 | Rofougaran et al. |
| 2017/0235126 A1 | 8/2017 | DiDomenico |
| 2017/0235129 A1 | 8/2017 | Kamakura |
| 2017/0235142 A1 | 8/2017 | Wall et al. |
| 2017/0235144 A1 | 8/2017 | Piskunov et al. |
| 2017/0235147 A1 | 8/2017 | Kamakura |
| 2017/0243403 A1 | 8/2017 | Daniels et al. |
| 2017/0246070 A1 | 8/2017 | Osterhout et al. |
| 2017/0254832 A1 | 9/2017 | Ho et al. |
| 2017/0256096 A1 | 9/2017 | Faaborg et al. |
| 2017/0258526 A1 | 9/2017 | Lang |
| 2017/0266529 A1 | 9/2017 | Reikmoto |
| 2017/0270712 A1 | 9/2017 | Tyson et al. |
| 2017/0281054 A1 | 10/2017 | Stever et al. |
| 2017/0287376 A1 | 10/2017 | Bakar et al. |
| 2017/0293141 A1 | 10/2017 | Schowengerdt et al. |
| 2017/0307886 A1 | 10/2017 | Stenberg et al. |
| 2017/0307891 A1 | 10/2017 | Bucknor et al. |
| 2017/0312032 A1 | 11/2017 | Amanatullah et al. |
| 2017/0322418 A1 | 11/2017 | Liu et al. |
| 2017/0322426 A1 | 11/2017 | Tervo |
| 2017/0329137 A1 | 11/2017 | Tervo |
| 2017/0332098 A1 | 11/2017 | Rusanovskyy et al. |
| 2017/0336636 A1 | 11/2017 | Amitai et al. |
| 2017/0336867 A1 | 11/2017 | Wilairat et al. |
| 2017/0357332 A1 | 12/2017 | Balan et al. |
| 2017/0363871 A1 | 12/2017 | Vallius |
| 2017/0371394 A1 | 12/2017 | Chan |
| 2017/0371661 A1 | 12/2017 | Sparling |
| 2018/0014266 A1 | 1/2018 | Chen |
| 2018/0024289 A1 | 1/2018 | Fattal |
| 2018/0039673 A1 | 2/2018 | Chen et al. |
| 2018/0044173 A1 | 2/2018 | Netzer |
| 2018/0052007 A1 | 2/2018 | Teskey et al. |
| 2018/0052501 A1 | 2/2018 | Jones, Jr. et al. |
| 2018/0056305 A1 | 3/2018 | Sankey et al. |
| 2018/0059305 A1 | 3/2018 | Popovich et al. |
| 2018/0067779 A1 | 3/2018 | Pillalamarri et al. |
| 2018/0070855 A1 | 3/2018 | Eichler |
| 2018/0082480 A1 | 3/2018 | White et al. |
| 2018/0084245 A1 | 3/2018 | Lapstun |
| 2018/0088185 A1 | 3/2018 | Woods et al. |
| 2018/0101214 A1 | 4/2018 | Mahindru et al. |
| 2018/0102981 A1 | 4/2018 | Kurtzman et al. |
| 2018/0108179 A1 | 4/2018 | Tomlin et al. |
| 2018/0114298 A1 | 4/2018 | Malaika et al. |
| 2018/0129112 A1 | 5/2018 | Osterhout |
| 2018/0131907 A1 | 5/2018 | Schmirler et al. |
| 2018/0136466 A1 | 5/2018 | Ko |
| 2018/0144691 A1 | 5/2018 | Choi et al. |
| 2018/0150971 A1 | 5/2018 | Adachi et al. |
| 2018/0151796 A1 | 5/2018 | Akahane |
| 2018/0172995 A1 | 6/2018 | Lee et al. |
| 2018/0188115 A1 | 7/2018 | Hsu et al. |
| 2018/0189568 A1 | 7/2018 | Powderly et al. |
| 2018/0190017 A1 | 7/2018 | Mendez et al. |
| 2018/0191990 A1 | 7/2018 | Motoyama et al. |
| 2018/0196084 A1 | 7/2018 | Tustaniwskyj |
| 2018/0217395 A1 | 8/2018 | Lin et al. |
| 2018/0218545 A1 | 8/2018 | Garcia et al. |
| 2018/0250589 A1 | 9/2018 | Cossairt et al. |
| 2018/0260218 A1 | 9/2018 | Gopal |
| 2018/0284877 A1 | 10/2018 | Klein |
| 2018/0292654 A1 | 10/2018 | Wall et al. |
| 2018/0299678 A1 | 10/2018 | Singer et al. |
| 2018/0357472 A1 | 12/2018 | Dreessen |
| 2019/0005069 A1 | 1/2019 | Filgueiras de Araujo et al. |
| 2019/0011691 A1 | 1/2019 | Peyman |
| 2019/0056591 A1 | 2/2019 | Tervo et al. |
| 2019/0087015 A1 | 3/2019 | Lam et al. |
| 2019/0101758 A1 | 4/2019 | Zhu et al. |
| 2019/0107723 A1 | 4/2019 | Lee et al. |
| 2019/0137788 A1 | 5/2019 | Suen |
| 2019/0155034 A1 | 5/2019 | Singer et al. |
| 2019/0155439 A1 | 5/2019 | Mukherjee et al. |
| 2019/0158926 A1 | 5/2019 | Kang et al. |
| 2019/0162950 A1 | 5/2019 | Lapstun |
| 2019/0167095 A1 | 6/2019 | Krueger |
| 2019/0171909 A1 | 6/2019 | Mandal et al. |
| 2019/0172216 A1 | 6/2019 | Ninan et al. |
| 2019/0178654 A1 | 6/2019 | Hare |
| 2019/0179654 A1 | 6/2019 | Hare |
| 2019/0182415 A1 | 6/2019 | Sivan |
| 2019/0196690 A1 | 6/2019 | Chong et al. |
| 2019/0206116 A1 | 7/2019 | Xu et al. |
| 2019/0219815 A1 | 7/2019 | Price et al. |
| 2019/0243123 A1 | 8/2019 | Bohn |
| 2019/0287270 A1 | 9/2019 | Nakamura et al. |
| 2019/0307510 A1 | 10/2019 | Rotenberg et al. |
| 2019/0318502 A1 | 10/2019 | He et al. |
| 2019/0318540 A1 | 10/2019 | Piemonte et al. |
| 2019/0321728 A1 | 10/2019 | Imai et al. |
| 2019/0347853 A1 | 11/2019 | Chen et al. |
| 2019/0380792 A1 | 12/2019 | Poltaretskyi et al. |
| 2019/0388182 A1 | 12/2019 | Kumar et al. |
| 2020/0066045 A1 | 2/2020 | Stahl et al. |
| 2020/0098188 A1 | 3/2020 | Bar-Zeev et al. |
| 2020/0100057 A1 | 3/2020 | Galon et al. |
| 2020/0110928 A1 | 4/2020 | Al Jazaery et al. |
| 2020/0117267 A1 | 4/2020 | Gibson et al. |
| 2020/0117270 A1 | 4/2020 | Gibson et al. |
| 2020/0184217 A1 | 6/2020 | Faulkner |
| 2020/0184653 A1 | 6/2020 | Faulker |
| 2020/0202759 A1 | 6/2020 | Ukai et al. |
| 2020/0242848 A1 | 7/2020 | Ambler et al. |
| 2020/0309944 A1 | 10/2020 | Thoresen et al. |
| 2020/0356161 A1 | 11/2020 | Wagner |
| 2020/0368616 A1 | 11/2020 | Delamont |
| 2020/0391115 A1 | 12/2020 | Leeper et al. |
| 2020/0409528 A1 | 12/2020 | Lee |
| 2021/0008413 A1 | 1/2021 | Asikainen et al. |
| 2021/0033871 A1 | 2/2021 | Jacoby et al. |
| 2021/0041951 A1 | 2/2021 | Gibson et al. |
| 2021/0053820 A1 | 2/2021 | Gurin et al. |
| 2021/0093391 A1 | 4/2021 | Poltaretskyi et al. |
| 2021/0093410 A1 | 4/2021 | Gaborit et al. |
| 2021/0093414 A1 | 4/2021 | Moore et al. |
| 2021/0097886 A1 | 4/2021 | Kuester et al. |
| 2021/0124901 A1 | 4/2021 | Liu et al. |
| 2021/0132380 A1 | 5/2021 | Wieczorek |
| 2021/0141225 A1 | 5/2021 | Meynen et al. |
| 2021/0142582 A1 | 5/2021 | Jones et al. |
| 2021/0150264 A1 | 5/2021 | Karanam |
| 2021/0158023 A1 | 5/2021 | Fu et al. |
| 2021/0158627 A1 | 5/2021 | Cossairt et al. |
| 2021/0173480 A1 | 6/2021 | Osterhout et al. |
| 2021/0319236 A1 | 10/2021 | Tang |
| 2021/0333551 A1 | 10/2021 | Schultz |
| 2022/0366598 A1 | 11/2022 | Azimi et al. |
| 2023/0351808 A1 | 11/2023 | Jarvenpaa |
| 2023/0384593 A1 | 11/2023 | Ofir |
| 2024/0103212 A1 | 3/2024 | Jarvenpaa |
| 2025/0039342 A1 | 1/2025 | Traczyk et al. |
| 2025/0189802 A1 | 6/2025 | Ofir |

FOREIGN PATENT DOCUMENTS

| | | |
|---|---|---|
| CN | 102448566 A | 5/2012 |
| CN | 103460255 A | 12/2013 |
| CN | 104040410 A | 9/2014 |
| CN | 104603675 A | 5/2015 |
| CN | 105938426 A | 9/2016 |
| CN | 106662754 A | 5/2017 |
| CN | 107004303 A | 8/2017 |
| CN | 107683497 A1 | 2/2018 |
| CN | 109223121 A | 1/2019 |
| CN | 105190427 B | 11/2019 |
| EP | 0504930 A1 | 3/1992 |
| EP | 0535402 A1 | 4/1993 |
| EP | 0632360 A1 | 1/1995 |
| EP | 1215522 A2 | 6/2002 |
| EP | 13451682 A2 | 2/2003 |
| EP | 1494110 A2 | 1/2005 |

(56) References Cited

FOREIGN PATENT DOCUMENTS

| | | | |
|---|---|---|---|
| EP | 1938141 A1 | 7/2008 | |
| EP | 1943556 A2 | 7/2008 | |
| EP | 2290428 A2 | 3/2011 | |
| EP | 2350774 A1 | 8/2011 | |
| EP | 2818910 A1 * | 12/2014 | ......... G02B 27/4272 |
| EP | 1237067 B1 | 1/2016 | |
| EP | 3139245 A1 | 3/2017 | |
| EP | 3164776 B1 | 5/2017 | |
| EP | 3236211 A1 | 10/2017 | |
| EP | 2723240 B1 | 8/2018 | |
| EP | 2896986 B1 | 2/2021 | |
| GB | 2499635 A | 8/2013 | |
| GB | 2542853 A | 4/2017 | |
| IN | 938/DEL/2004 | 6/2006 | |
| JP | H03-036974 U | 4/1991 | |
| JP | 09-121370 A | 5/1997 | |
| JP | H10-333094 A | 12/1998 | |
| JP | 2002-015222 A | 1/2002 | |
| JP | 2002-529806 | 9/2002 | |
| JP | 2003-029198 A | 1/2003 | |
| JP | 2003-141574 A | 5/2003 | |
| JP | 2003-228027 A | 8/2003 | |
| JP | 2003-329873 A | 11/2003 | |
| JP | 2004-348169 A | 12/2004 | |
| JP | 2005-151224 A | 6/2005 | |
| JP | 2005-303843 A | 10/2005 | |
| JP | 2007-012530 A | 1/2007 | |
| JP | 2007-86696 A | 4/2007 | |
| JP | 2007-273733 A | 10/2007 | |
| JP | 2008-257127 A | 10/2008 | |
| JP | 2009-090689 A | 4/2009 | |
| JP | 2009-244869 A | 10/2009 | |
| JP | 2010-014443 A | 1/2010 | |
| JP | 2010-139575 | 6/2010 | |
| JP | 2010-146030 A | 7/2010 | |
| JP | 2010-526341 A | 7/2010 | |
| JP | 2010-271526 A | 12/2010 | |
| JP | 2011-033993 A | 2/2011 | |
| JP | 2011-504522 A | 2/2011 | |
| JP | 2011-257203 A | 12/2011 | |
| JP | 2011-530131 A | 12/2011 | |
| JP | 2012-8356 A | 1/2012 | |
| JP | 2012-015774 A | 1/2012 | |
| JP | 2012-088777 A | 5/2012 | |
| JP | 2012-235036 A | 11/2012 | |
| JP | 2013-525872 A1 | 6/2013 | |
| JP | 2013-206322 A | 10/2013 | |
| JP | 2013-250045 A | 12/2013 | |
| JP | 2014-500522 A | 1/2014 | |
| JP | 2014-068465 A | 4/2014 | |
| JP | 2014-90386 A | 5/2014 | |
| JP | 2014-174366 A | 9/2014 | |
| JP | 2014-524229 A | 9/2014 | |
| JP | 2014-192550 A | 10/2014 | |
| JP | 2015-156512 A | 8/2015 | |
| JP | 2015-191032 A | 11/2015 | |
| JP | 2016-502120 A | 1/2016 | |
| JP | 2016-85463 A | 5/2016 | |
| JP | 2016-516227 A | 6/2016 | |
| JP | 2016-126134 A | 7/2016 | |
| JP | 2017-015697 A | 1/2017 | |
| JP | 2017-108444 A | 6/2017 | |
| JP | 2017-153498 | 9/2017 | |
| JP | 2017-531840 A | 10/2017 | |
| JP | 2017-535825 A | 11/2017 | |
| JP | 6232763 B2 | 11/2017 | |
| JP | 2018-503165 A | 2/2018 | |
| JP | 6333965 B2 | 5/2018 | |
| JP | 2018-173739 A | 11/2018 | |
| JP | 2019-177134 A | 10/2019 | |
| JP | 7344896 B2 | 9/2023 | |
| KR | 2005-0010775 A | 1/2005 | |
| KR | 10-2006-0059992 A | 6/2006 | |
| KR | 10-2011-0006408 | 1/2011 | |
| KR | 10-1372623 B1 | 3/2014 | |
| KR | 10-2017-0017243 | 2/2017 | |
| TW | 201219829 A | 5/2012 | |
| TW | 201803289 A | 1/2018 | |
| WO | 1991/000565 A2 | 1/1991 | |
| WO | 2000/030368 A1 | 6/2000 | |
| WO | 2004095248 A | 11/2004 | |
| WO | 2006132614 A1 | 12/2006 | |
| WO | 2007037089 A1 | 4/2007 | |
| WO | 2007041678 A2 | 4/2007 | |
| WO | 2007/085628 A1 | 8/2007 | |
| WO | 2007/102144 A1 | 9/2007 | |
| WO | 2008137299 A1 | 11/2008 | |
| WO | 2008148927 A1 | 12/2008 | |
| WO | 2009060125 A1 | 5/2009 | |
| WO | 2009/101238 A1 | 8/2009 | |
| WO | 2010015807 A1 | 2/2010 | |
| WO | 2014203440 A1 | 12/2010 | |
| WO | 2012030787 A2 | 3/2012 | |
| WO | 2013/049012 A1 | 4/2013 | |
| WO | 2013062701 A1 | 5/2013 | |
| WO | 2013/145536 A1 | 10/2013 | |
| WO | 2014033306 A1 | 3/2014 | |
| WO | 2015/079610 A1 | 6/2015 | |
| WO | 2015143641 A1 | 10/2015 | |
| WO | 2015194597 A1 | 12/2015 | |
| WO | 2016/054092 A1 | 4/2016 | |
| WO | 2017004695 A1 | 1/2017 | |
| WO | 2017044761 A1 | 3/2017 | |
| WO | 2017049163 A1 | 3/2017 | |
| WO | 2017051595 A1 | 3/2017 | |
| WO | 2017120475 A1 | 7/2017 | |
| WO | 2017176861 A1 | 10/2017 | |
| WO | 2017203201 A1 | 11/2017 | |
| WO | 2018008232 A1 | 1/2018 | |
| WO | 2018/031261 A1 | 2/2018 | |
| WO | 2018022523 A1 | 2/2018 | |
| WO | 2018/044537 A1 | 3/2018 | |
| WO | 2018039273 A1 | 3/2018 | |
| WO | 2018057564 A1 | 3/2018 | |
| WO | 2018085287 A1 | 5/2018 | |
| WO | 2018087408 A1 | 5/2018 | |
| WO | 2018097831 A1 | 5/2018 | |
| WO | 2018/166921 A | 9/2018 | |
| WO | 2018166921 A1 | 9/2018 | |
| WO | 2018236587 A1 | 12/2018 | |
| WO | 2019040493 A1 | 2/2019 | |
| WO | 2016075689 A1 | 5/2019 | |
| WO | 2019148154 A1 | 8/2019 | |
| WO | 2020010226 A1 | 1/2020 | |

OTHER PUBLICATIONS

"Communication according to Rule 164(1) EPC mailed on Feb. 23, 2022" , European Patent Application No. 20753144.3 , (11 pages).

"Communication Pursuant to Article 94(3) EPC mailed on Sep. 4, 2019" , European Patent Application No. 10793707.0 , (4 pages).

"Communication Pursuant to Article 94(3) EPC mailed on Apr. 25, 2022" , European Patent Application No. 18885707.2 , (5 pages).

"Communication Pursuant to Article 94(3) EPC mailed on Jan. 4, 2022" , European Patent Application No. 20154070.5 , (8 pages).

"Communication Pursuant to Article 94(3) EPC mailed on May 30, 2022" , European Patent Application No. 19768418.6 , (6 pages).

"Communication Pursuant to Article 94(3) EPC mailed on Oct. 21, 2021" , European Patent Application No. 16207441.3 , (4 pages).

"Communication Pursuant to Rule 164(1) EPC mailed on Feb. 23, 2022" , European Patent Application No. 20753144.3 , (11 pages).

"Communication Pursuant to Rule 164(1) EPC mailed on Jul. 27, 2021" , European Patent Application No. 19833664.6 , (11 pages).

"Decision of Rejection mailed on Jan. 5, 2023 with English translation" , Chinese Patent Application No. 201880079474.6 , (10 pages).

"European Search Report mailed on Oct. 15, 2020" , European Patent Application No. 20180623.9 , (10 pages).

"Extended European Search Report issued on Apr. 5, 2023" , European Patent Application No. 20888716.6 , (11 pages).

"Extended European Search Report issued on Dec. 14, 2022" , European Patent Application No. 20886547.7 , (8 pages).

(56)　　　　References Cited

OTHER PUBLICATIONS

"Extended European Search Report issued on May 20, 2020" , European Patent Application No. 20154070.5 , (7 pages).
"Extended European Search Report issued on Jan. 22, 2021" , European Patent Application No. 18890390.0 , (11 pages).
"Extended European Search Report issued on Nov. 3, 2020" , European Patent Application No. 18885707.2 , (7 pages).
"Extended European Search Report issued on Jun. 30, 2021" , European Patent Application No. 19811971.1 , (9 pages).
"Extended European Search Report issued on Mar. 4, 2021" , European Patent Application No. 19768418.6 , (9 pages).
"Extended European Search Report issued on Nov. 4, 2020" , European Patent Application No. 20190980.1 , (14 pages).
"Extended European Search Report issued on Aug. 24, 2022" , European Patent Application No. 20846338.0 , (13 pages).
"Extended European Search Report issued on Aug. 8, 2022" , European Patent Application No. 19898874.3 , (8 pages).
"Extended European Search Report issued on Sep. 8, 2022" , European Patent Application No. 20798769.4 , (13 pages).
"Extended European Search Report mailed on Nov. 3, 2022" , European Patent Application No. 20770244.0 , (23 pages).
"Extended European Search Report mailed on Jun. 12, 2017" , European Patent Application No. 16207441.3 , (8 pages).
"Extended European Search Report mailed on Jan. 28, 2022" , European Patent Application No. 19815876.8 , (9 pages).
"Extended European Search Report mailed on Jan. 4, 2022" , European Patent Application No. 19815085.6 , (9 pages).
"Extended European Search Report mailed on Jul. 16, 2021" , European Patent Application No. 19810142.0 , (14 pages).
"Extended European Search Report mailed on Jul. 30, 2021" , European Patent Application No. 19839970.1 , (7 pages).
"Extended European Search Report mailed on Jun. 19, 2020" , European Patent Application No. 20154750.2 , (10 pages).
"Extended European Search Report mailed on Mar. 22, 2022" , European Patent Application No. 19843487.0 , (14 pages).
"Extended European Search Report mailed on May 16, 2022" , European Patent Application No. 19871001.4 , (9 pages).
"Extended European Search Report mailed on May 30, 2022" , European Patent Application No. 20753144.3 , (10 pages).
"Extended European Search Report mailed on Oct. 27, 2021" , European Patent Application No. 19833664.6 , (10 pages).
"Extended European Search Report mailed on Sep. 20, 2021" , European Patent Application No. 19851373.1 , (8 pages).
"Extended European Search Report mailed on Sep. 28, 2021" , European Patent Application No. 19845418.3 , (13 pages).
"Final Office Action mailed on Aug. 10, 2020" , U.S. Appl. No. 16/225,961 , (13 pages).
"Final Office Action mailed on Dec. 29, 2022" , U.S. Appl. No. 17/098,059 , (32 pages).
"Final Office Action mailed on Dec. 4, 2019" , U.S. Appl. No. 15/564,517 , (15 pages).
"Final Office Action mailed on Feb. 19, 2020" , U.S. Appl. No. 15/552,897 , (17 pages).
"Final Office Action mailed on Feb. 23, 2022" , U.S. Appl. No. 16/748,193 , (23 pages).
"Final Office Action mailed on Feb. 3, 2022" , U.S. Appl. No. 16/864,721 , (36 pages).
"Final Office Action mailed on Jul. 13, 2022" , U.S. Appl. No. 17/262,991 , (18 pages).
"Final Office Action mailed on Jun. 15, 2021" , U.S. Appl. No. 16/928,313 , (42 pages).
"Final Office Action mailed on Mar. 1, 2021" , U.S. Appl. No. 16/214,575 , (29 pages).
"Final Office Action mailed on Mar. 10, 2023" , U.S. Appl. No. 17/357,795 , (15 pages).
"Final Office Action mailed on Mar. 19, 2021" , U.S. Appl. No. 16/530,776 , (25 pages).
"Final Office Action mailed on Nov. 24, 2020" , U.S. Appl. No. 16/435,933 , (44 pages).
"Final Office Action mailed on Sep. 17, 2021" , U.S. Appl. No. 16/938,782 , (44 pages).
"First Examination Report Mailed on Jul. 27, 2022" , Chinese Patent Application No. 201980036675.2 , (5 pages).
"First Examination Report Mailed on Jul. 28, 2022" , Indian Patent Application No. 202047024232 , (6 pages).
"First Examination Report Mailed on May 13, 2022" , Indian Patent Application No. 202047026359 , (8 pages).
"First Office Action mailed Apr. 21, 2023 with English translation" , Japanese Patent Application No. 2021-509779 , (26 pages).
"First Office Action mailed on Dec. 22, 2022 with English translation" , Chinese Patent Application No. 201980061450.2 , (11 pages).
"First Office Action mailed on Jan. 24, 2023 with English translation" , Japanese Patent Application No. 2020-549034 , (7 pages).
"First Office Action mailed on Jan. 30, 2023 with English translation" , Chinese Patent Application No. 201980082951.9 , (5 pages).
"First Office Action mailed on Jun. 13, 2023 with English translation" , Japanese Patent Application No. 2020-567853 , (7 pages).
"First Office Action mailed on Mar. 14, 2022 with English translation" , Chinese Patent Application No. 201880079474.6 , (11 pages).
"First Office Action mailed on Mar. 27, 2023 with English translation" , Japanese Patent Application No. 2020-566617 , (6 pages).
"First Office Action mailed on Mar. 6, 2023 with English translation" , Korean Patent Application No. 10-2020-7019685 , (7 pages).
"First Office Action mailed on May 26, 2023 with English translation" , Japanese Patent Application No. 2021-500607 , (6 pages).
"First Office Action mailed on May 30, 2023 with English translation" , Japanese Patent Application No. 2021-519873 , (8 pages).
"FS_XR5G: Permanent document, v0.4.0" , Qualcomm Incorporated, 3GPP TSG-SA 4 Meeting 103 retrieved from the Internet: URL:http://www.3gpp.org/ftp/Meetings%5F3GPP%5FSYNC/SA4/ Docs/S4%2DI90526%2Ezip [retrieved on Apr. 12, 2019] , Apr. 12, 2019 , (98 pages).
"International Search Report and Written Opinion mailed on Feb. 12, 2021" , International PCT Application No. PCT/US20/60555 , (25 pages).
"International Search Report and Written Opinion mailed on Mar. 12, 2020" , International PCT Patent Application No. PCT/US19/ 67919 , (14 pages).
"International Search Report and Written Opinion mailed on Aug. 15, 2019" , International PCT Patent Application No. PCT/US19/ 33987 , (20 pages).
"International Search Report and Written Opinion mailed on Jun. 15, 2020" , International PCT Patent Application No. PCT/US2020/ 017023 , (13 pages).
"International Search Report and Written Opinion mailed on Oct. 16, 2019" , International PCT Patent Application No. PCT/US19/ 43097 , (10 pages).
"International Search Report and Written Opinion mailed on Oct. 16, 2019" , International PCT Patent Application No. PCT/US19/ 36275 , (10 pages).
"International Search Report and Written Opinion mailed on Oct. 16, 2019" , International PCT Patent Application No. PCT/US19/ 43099 , (9 pages).
"International Search Report and Written Opinion mailed on Jun. 17, 2016" , International PCT Patent Application No. PCT/FI2016/ 050172 , (9 pages).
"International Search Report and Written Opinion mailed on Feb. 2, 2021" , International PCT Patent Application No. PCT/US20/60550 , (9 pages).
"International Search Report and Written Opinion mailed on Oct. 22, 2019" , International PCT Patent Application No. PCT/US19/ 43751 , (9 pages).
"International Search Report and Written Opinion mailed on Dec. 23, 2019" , International PCT Patent Application No. PCT/US19/ 44953 , (11 pages).
"International Search Report and Written Opinion mailed on May 23, 2019" , International PCT Patent Application No. PCT/US18/ 66514 , (17 pages).

(56) References Cited

OTHER PUBLICATIONS

"International Search Report and Written Opinion mailed on Sep. 26, 2019" , International PCT Patent Application No. PCT/US19/40544 , (12 pages).

"International Search Report and Written Opinion mailed on Aug. 27, 2019" , International PCT Application No. PCT/US2019/035245 , (8 pages).

"International Search Report and Written Opinion mailed on Dec. 27, 2019" , International PCT Application No. PCT/US19/47746 , (16 pages).

"International Search Report and Written Opinion mailed on Dec. 3, 2020" , International PCT Patent Application No. PCT/US20/43596 , (25 pages).

"International Search Report and Written Opinion mailed on Sep. 30, 2019" , International PCT Patent Application No. PCT/US19/40324 , (7 pages).

"International Search Report and Written Opinion mailed on Sep. 4, 2020" , International PCT Patent Application No. PCT/US20/31036 , (13 pages).

"International Search Report and Written Opinion mailed on Jun. 5, 2020" , International PCT Patent Application No. PCT/US20/19871 , (9 pages).

"International Search Report and Written Opinion mailed on Aug. 8, 2019" , International PCT Patent Application No. PCT/US2019/034763 , (8 pages).

"International Search Report and Written Opinion mailed on Oct. 8, 2019" , International PCT Patent Application No. PCT/US19/41151 , (7 pages).

"International Search Report and Written Opinion mailed on Jan. 9, 2020" , International PCT Application No. PCT/US19/55185 , (10 pages).

"International Search Report and Written Opinion mailed on Feb. 7, 2020" , International PCT Patent Application No. PCT/US2019/061265 , (11 pages).

"International Search Report and Written Opinion mailed on Jun. 11, 2019" , International PCT Application No. PCT/US19/22620 , (7 pages).

"Invitation to Pay Additional Fees mailed Aug. 15, 2019" , International PCT Patent Application No. PCT/US19/36275 , (2 pages).

"Invitation to Pay Additional Fees mailed Sep. 24, 2020" , International PCT Patent Application No. PCT/US2020/043596 , (3 pages).

"Invitation to Pay Additional Fees mailed on Oct. 22, 2019" , International PCT Patent Application No. PCT/US19/47746 , (2 pages).

"Invitation to Pay Additional Fees mailed on Apr. 3, 2020" , International PCT Patent Application No. PCT/US20/17023 , (2 pages).

"Invitation to Pay Additional Fees mailed on Oct. 17, 2019" , International PCT Patent Application No. PCT/US19/44953 , (2 pages).

"Multi-core processor" , TechTarget , 2013 , (1 page).

"Non Final Office Action mailed Nov. 19. 2019" , U.S. Appl. No. 16/355,611 , (31 pages).

"Non Final Office Action mailed on Apr. 1, 2022" , U.S. Appl. No. 17/256,961 , (65 pages).

"Non Final Office Action mailed on Apr. 11, 2022" , U.S. Appl. No. 16/938,782 , (52 pages).

"Non Final Office Action mailed on Apr. 12, 2022" , U.S. Appl. No. 17/262,991 , (60 pages).

"Non Final Office Action mailed on Apr. 13, 2023" , U.S. Appl. No. 17/098,043 , (7 pages).

"Non Final Office Action mailed on Aug. 21, 2019" , U.S. Appl. No. 15/564,517 , (14 pages).

"Non Final Office Action mailed on Aug. 4, 2021" , U.S. Appl. No. 16/864,721 , (21 pages).

"Non Final Office Action mailed on Dec. 7, 2022" , U.S. Appl. No. 17/357,795 , (63 pages).

"Non Final Office Action mailed on Feb. 2, 2022" , U.S. Appl. No. 16/783,866 , (8 pages).

"Non Final Office Action mailed on Feb. 3, 2023" , U.S. Appl. No. 17/429,100 , (16 pages).

"Non Final Office Action mailed on Feb. 3, 2023" , U.S. Appl. No. 17/497,965 , (32 pages).

"Non Final Office Action mailed on Jan. 24, 2023" , U.S. Appl. No. 17/497,940 , (10 pages).

"Non Final Office Action mailed on Jan. 26, 2021" , U.S. Appl. No. 16/928,313 , (33 pages).

"Non Final Office Action mailed on Jan. 27, 2021" , U.S. Appl. No. 16/225,961 , (15 pages).

"Non Final Office Action mailed on Jul. 26, 2022" , U.S. Appl. No. 17/098,059 , (28 pages).

"Non Final Office Action mailed on Jul. 27, 2020" , U.S. Appl. No. 16/435,933 , (16 pages).

"Non Final Office Action mailed on Jul. 9, 2021" , U.S. Appl. No. 17/002,663 , (43 pages).

"Non Final Office Action mailed on Jul. 9, 2021" , U.S. Appl. No. 16/833,093 , (47 pages).

"Non Final Office Action mailed on Jun. 10, 2021" , U.S. Appl. No. 16/938,782 , (40 Pages).

"Non Final Office Action mailed on Jun. 17, 2020" , U.S. Appl. No. 16/682,911 , (22 pages).

"Non Final Office Action mailed on Jun. 19, 2020" , U.S. Appl. No. 16/225,961 , (35 pages).

"Non Final Office Action mailed on Jun. 29, 2021" , U.S. Appl. No. 16/698,588 , (58 pages).

"Non Final Office Action mailed on Mar. 1, 2023" , U.S. Appl. No. 18/046,739 , (34 pages).

"Non Final Office Action mailed on Mar. 3, 2021" , U.S. Appl. No. 16/427,337 , (41 pages).

"Non Final Office Action mailed on Mar. 31, 2022" , U.S. Appl. No. 17/257,814 , (60 pages).

"Non Final Office Action mailed on Mar. 9, 2022" , U.S. Appl. No. 16/870,676 , (57 pages).

"Non Final Office Action mailed on May 10, 2022" , U.S. Appl. No. 17/140,921 , (25 pages).

"Non Final Office Action mailed on May 11, 2023" , U.S. Appl. No. 17/822,279 , (24 pages).

"Non Final Office Action mailed on May 17, 2022" , U.S. Appl. No. 16/748,193 , (11 pages).

"Non Final Office Action mailed on May 26, 2021" , U.S. Appl. No. 16/214,575 , (19 pages).

"Non Final Office Action mailed on Nov. 19, 2019" , U.S. Appl. No. 16/355,611 , (31 pages).

"Non Final Office Action mailed on Nov. 5, 2020" , U.S. Appl. No. 16/530,776 , (45 pages).

"Non Final Office Action mailed on Oct. 22, 2019" , U.S. Appl. No. 15/859,277 , (15 pages).

"Non Final Office Action mailed on Sep. 1, 2020" , U.S. Appl. No. 16/214,575 , (40 pages).

"Non Final Office Action mailed on Sep. 19, 2022" , U.S. Appl. No. 17/263,001 , (14 pages).

"Non Final Office Action mailed on Sep. 20, 2021" , U.S. Appl. No. 17/105,848 , (56 pages).

"Non Final Office Action mailed on Sep. 29, 2021" , U.S. Appl. No. 16/748,193 , (62 pages).

"Notice of Allowance mailed on Mar. 25, 2020" , U.S. Appl. No. 15/564,517 , (11 pages).

"Notice of Allowance mailed on Oct. 5, 2020" , U.S. Appl. No. 16/682,911 , (27 pages).

"Notice of Reason for Rejection mailed on Oct. 28, 2022 with English translation" , Japanese Patent Application No. 2020-531452 , (3 pages).

"Notice of Reason of Refusal mailed on Sep. 11, 2020 with English translation" , Japanese Patent Application No. 2019-140435 , (6 pages).

"Office Action mailed on Jun. 8, 2023 with English translation" , Japanese Patent Application No. 2021-503762 , (6 pages).

"Office Action mailed on Mar. 30, 2023 with English translation" , Japanese Patent Application No. 2020-566620 , (10 pages).

"Office Action mailed on Nov. 24, 2022 with English Translation" , Japanese Patent Application No. 2020-533730 , (11 pages).

(56) References Cited

OTHER PUBLICATIONS

"Phototourism Challenge", CVPR 2019 Image Matching Workshop. https://image matching-workshop. github.io. , (16 pages).

"Second Office Action mailed on Jul. 13, 2022 with English Translation" , Chinese Patent Application No. 201880079474.6 , (10 pages).

"Second Office Action mailed on Jun. 20, 2022 with English Translation" , Chinese Patent Application No. 201880089255.6 , (14 pages).

"Second Office Action mailed on May 2, 2023 with English Translation" , Japanese Patent Application No. 2020-549034 , (6 pages).

"Summons to attend oral proceedings pursuant to Rule 115(1) EPC mailed on Jul. 15, 2019" , European Patent Application No. 15162521.7 , (7 pages).

Aarik, J. , et al. , "Effect of crystal structure on optical properties of TiO2 films grown by atomic layer deposition" , Thin Solid Films; Publication [online]. May 19, 1998 [retrieved Feb. 19, 2020]. Retrieved from the Internet: <URL: https://www.sciencedirect.com/science/article/pii/S0040609097001351 ?via%3Dihub>; DOI: 10.1016/S0040-6090(97)00135-1; see entire document , (2 pages).

Altwaijry , et al. , "Learning to Detect and Match Keypoints with Deep Architectures" , Proceedings of the British Machine Vision Conference (BMVC), BMVA Press, Sep. 2016, [retrieved on Jan. 8, 2021 (Aug. 1, 2021 )] < URL: http://www.bmva.org/bmvc/2016/papers/paper049/index.html >, en lire document, especially Abstract.

Anonymous , "Koi Pond: Top iPhone App Store Paid App" , https://web.archive.org/web/20080904061233/https://www.iphoneincanada.ca/reviews /koi-pond-top-iphone-app-store-paid-app/—[retrieved on Aug. 9, 2022].

Arandjelović, Relja , et al. , "Three things everyone should know to improve object retrieval" , CVPR, 2012 , (8 pages).

Azom , "Silica—Silicon Dioxide (SiO2)" , AZO Materials; Publication [Online]. Dec. 13, 2001 [retrieved Feb. 19, 2020]. Retrieved from the Internet: <URL: https://www.azom.com/article.aspx?ArticleID=1114>.

Azuma, Ronald T. , "A Survey of Augmented Reality" , Presence: Teleoperators and Virtual Environments 6, 4 (Aug. 1997), 355-385; https://web.archive.org/web/20010604100006/http://www.cs.unc.edu/~azuma/ARpresence.pdf (downloaded Oct. 26, 2020).

Azuma, Ronald T. , "Predictive Tracking for Augmented Reality" , Department of Computer Science, Chapel Hill NC; TR95-007, Feb. 1995 , 262 pages.

Battaglia, Peter W, et al. , "Relational inductive biases, deep learning, and graph networks" , arXiv:1806.01261, Oct. 17, 2018 , pp. 1-40.

Berg, Alexander C , et al. , "Shape matching and object recognition using low distortion correspondences" , In CVPR, 2005 , (8 pages).

Bian, Jiawang , et al. , "GMS: Grid-based motion statistics for fast, ultra-robust feature correspondence." , In CVPR (Conference on Computer Vision and Pattern Recognition), 2017 , (10 pages).

Bimber, Oliver , et al. , "Spatial Augmented Reality: Merging Real and Virtual Worlds" , https://web.media.mit.edu/~raskar/book/BimberRaskarAugmentedRealityBook.pdf; published by A K Peters/CRC Press (Jul. 31, 2005); eBook (3rd Edition, 2007) , (393 pages).

Brachmann, Eric , et al. , "Neural-Guided RANSAC: Learning Where to Sample Model Hypotheses", In ICCV (International Conference on Computer Vision ), arXiv:1905.04132v2 [cs.CV] Jul. 31, 2019 , (17 pages).

Butail , et al. , "Putting the fish in the fish tank: Immersive VR for animal behavior experiments" , In: 2012 IEEE International Conference on Robotics and Automation. May 18, 2012 (May 18, 2012) Retrieved on Nov. 14, 2020 (Nov. 14, 2020) from <http:/lcdcl.umd.edu/papers/icra2012.pdf> entire document.

Caetano, Tibério S , et al. , "Learning graph matching" , IEEE TPAMI, 31(6):1048-1058, 2009.

Cech, Jan , et al. , "Efficient sequential correspondence selection by cosegmentation" , IEEE TPAMI, 32(9):1568-1581, Sep. 2010.

Chittineni, C. , et al. , "Single filters for combined image geometric manipulation and enhancement" , Proceedings of SPIE vol. 1903, Image and Video Processing, Apr. 8, 1993, San Jose, CA. (Year: 1993) , pp. 111-121.

Cuturi, Marco , "Sinkhorn distances: Lightspeed computation of optimal transport" , NIPS, 2013 , (9 pages).

Dai, Angela , et al. , "ScanNet: Richly-annotated 3d reconstructions of indoor scenes" , In CVPR, arXiv:1702.04405v2 [cs.CV] Apr. 11, 2017 , (22 pages).

Deng, Haowen , et al. , "PPFnet: Global context aware local features for robust 3d point matching" , In CVPR, arXiv: 1802.02669v2 [cs.CV] Mar. 1, 2018 , (12 pages).

Detone, Daniel , et al. , "Deep image homography estimation" , In RSS Work-shop: Limits and Potentials of Deep Learning in Robotics, arXiv:1606.03798v1 [cs.CV] Jun. 13, 2016 , (6 pages).

Detone, Daniel , et al. , "Self-improving visual odometry" , arXiv:1812.03245, Dec. 8, 2018 , (9 pages).

Detone, Daniel , et al. , "SuperPoint: Self-supervised interest point detection and description", In CVPR Workshop on Deep Learning for Visual SLAM, arXiv:1712.07629v4 [cs.CV] Apr. 19, 2018 , (13 pages).

Dusmanu, Mihai , et al. , "D2-net: A trainable CNN for joint detection and description of local features" , CVPR, arXiv:1905.03561v1 [cs.CV] May 9, 2019 , (16 pages).

Ebel, Patrick , et al. , "Beyond cartesian representations for local descriptors" , ICCV, arXiv:1908.05547v1 [cs.CV] Aug. 15, 2019 , (11 pages).

Fischler, Martin A , et al. , "Random sample consensus: a paradigm for model fitting with applications to image analysis and automated cartography" , Communications of the ACM, 24(6): 1981 , pp. 381-395.

Gilmer, Justin , et al. , "Neural message passing for quantum chemistry" , In ICML, arXiv: 1704.01212v2 [cs.LG] Jun. 12, 2017 , (14 pages).

Giuseppe, Donato , et al. , "Stereoscopic helmet mounted system for real time 3D environment reconstruction and indoor ego-motion estimation" , Proc. SPIE 6955, Head- and Helmet-Mounted Displays XIII: Design and Applications, SPIE Defense and Security Symposium, 2008, Orlando, Florida, United States , 69550P.

Goodfellow , "Titanium Dioxide—Titania (TiO2)" , AZO Materials; Publication [online]. Jan. 11, 2002 [retrieved Feb. 19, 2020]. Retrieved from the Internet: <URL: https://www.azom.com/article.aspx?ArticleID=1179>.

Hartley, Richard , et al. , "Multiple View Geometry in Computer Vision" , Cambridge University Press, 2003 , pp. 1-673.

Jacob, Robert J.K. , "Eye Tracking in Advanced Interface Design" , Human-Computer Interaction Lab, Naval Research Laboratory, Washington, D.C., date unknown. 2003 , pp. 1-50.

Lee , et al. , "Self-Attention Graph Pooling" , Cornell University Library/Computer Science/Machine Learning, Apr. 17, 2019 [retrieved on Jan. 8, 2021 from the Internet< URL: https://arxiv.org/abs/1904.08082 >, entire document.

Lee, Juho , et al. , "Set transformer: A frame-work for attention-based permutation-invariant neural networks" , ICML, arXiv:1810.00825v3 [cs.LG] May 26, 2019 , (17 pages).

Leordeanu, Marius , et al. , "A spectral technique for correspondence problems using pairwise constraints", Proceedings of (ICCV) International Conference on Computer Vision, vol. 2, pp. 1482-1489, Oct. 2005 , (8 pages).

Levola, T. , "Diffractive Optics for Virtual Reality Displays" , Journal of the SID EuroDisplay May 14, 2005, XP008093627, chapters 2-3, Figures 2 and 10 , pp. 467-475.

Levola, Tapani , "Invited Paper: Novel Diffractive Optical Components for Near to Eye Displays—Nokia Research Center", SID 2006 Digest, 2006 SID International Symposium, Society for Information Display, vol. XXXVII, May 24, 2005, chapters 1-3, figures 1 and 3 , pp. 64-67.

Li, Yujia , et al. , "Graph Matching Networks for Learning the Similarity of Graph Structured Objects" , arxiv.org, Cornell University Library, 201 Olin Library Cornell University Ithaca, NY 14853, XP081268608.

(56)     References Cited

OTHER PUBLICATIONS

Li, Yujia , et al. , "Graph matching networks for learning the similarity of graph structured objects" , ICML, arXiv:1904.12787v2 [cs.LG] May 12, 2019 , (18 pages).

Li, Zhengqi , et al. , "Megadepth: Learning single-view depth prediction from internet photos" , In CVPR, fromarXiv: 1804. 00607v4 [cs.CV] Nov. 28, 2018 , (10 pages).

Libovicky , et al. , "Input Combination Strategies for Multi-Source Transformer Decoder" , Proceedings of the Third Conference on Machine Translation (WMT). vol. 1: Research Papers, Belgium, Brussels, Oct. 31-Nov. 1, 2018; retrieved on Jan. 8, 2021 (Jan. 8, 2021 ) from < URL: https://doi.org/10.18653/v1/W18-64026 >, entire document.

Loiola, Eliane Maria, et al. , "A survey for the quadratic assignment problem" , European journal of operational research, 176(2): 2007 , pp. 657-690.

Lowe, David G , "Distinctive image features from scale- invariant keypoints" , International Journal of Computer Vision, 60(2): 91-110, 2004 , (28 pages).

Luo, Zixin , et al. , "ContextDesc: Local descriptor augmentation with cross-modality context" , CVPR, arXiv:1904.04084v1 [cs.CV] Apr. 8, 2019 , (14 pages).

Luo, Zixin , et al. , "ContextDesc: Local Descriptor Augmentation With Cross-Modality Context" , 2019 IEEE/CVF Conference on Computer Vision and Pattern Recognition (CVPR), IEEE, XP033686823, DOI: 10.1109/CVPR.2019.00263 [retrieved on Jan. 8, 2020] , pp. 2522-2531.

Memon, F. , et al. , "Synthesis, Characterization and Optical Constants of Silicon Oxycarbide" , EPJ Web of Conferences; Publication [online]. Mar. 23, 2017 [retrieved Feb. 19, 2020).<URL: https://www.epj-conferences.org/articles/epjconf/pdf/2017/08/epjconf_ nanop2017 _00002.pdf>; DOI: 10.1051/epjconf/201713900002 , (8 pages).

Molchanov, Pavlo , et al. , "Short-range FMCW monopulse radar for hand-gesture sensing" , 2015 IEEE Radar Conference (RadarCon) (2015) , pp. 1491-1496.

Mrad , et al. , "A framework for System Level Low Power Design Space Exploration" , 1991.

Munkres, James , "Algorithms for the assignment and transportation problems" , Journal of the Society for Industrial and Applied Mathematics, 5(1): 1957 , pp. 32-38.

Ono, Yuki , et al. , "LF-Net: Learning local features from images", 32nd Conference on Neural Information Processing Systems (NIPS 2018), arXiv: 1805.09662v2 [cs.CV] Nov. 22, 2018 , (13 pages).

Paszke, Adam , et al. , "Automatic differentiation in Pytorch" , 31st Conference on Neural Information Processing Systems (NIPS 2017), Long Beach, CA, USA , (4 pages).

Peyré, Gabriel , et al. , "Computational Optimal Transport" , Foundations and Trends in Machine Learning, 11(5-6):355-607, 2019; arXiv: 1803.00567v4 [stat.ML] Mar. 18, 2020 , (209 pages).

Qi, Charles Ruizhongtai, et al. , "Pointnet++: Deep hierarchical feature learning on point sets in a metric space.", 31st Conference on Neural Information Processing Systems (NIPS 2017), Long Beach, CA, USA., Jun. 7, 2017 , (10 pages).

Qi, Charles R , et al. , "Pointnet: Deep Learning on Point Sets for 3D Classification and Segmentation" , CVPR, arXiv:1612.00593v2 [cs.CV] Apr. 10, 2017 , (19 pages).

Radenović, Filip , et al. , "Revisiting Oxford and Paris: Large-Scale Image Retrieval Benchmarking" , CVPR, arXiv:1803.11285v1 [cs. CV] Mar. 29, 2018 , (10 pages).

Raguram, Rahul , et al. , "A comparative analysis of ransac techniques leading to adaptive real-time random sample consensus" , Computer Vision—ECCV 2008, 10th European Conference on Computer Vision, Marseille, France, Oct. 12-18, 2008, Proceedings, Part I , (15 pages).

Ranftl, René , et al. , "Deep fundamental matrix estimation" , European Conference on Computer Vision (ECCV), 2018 , (17 pages).

Revaud, Jerome , et al. , "R2D2: Repeatable and Reliable Detector and Descriptor" , In NeurIPS, arXiv:1906.06195v2 [cs.CV] Jun. 17, 2019 , (12 pages).

Rocco, Ignacio , et al. , "Neighbourhood Consensus Networks" , 32nd Conference on Neural Information Processing Systems (NeurIPS 2018), Montreal, Canada, arXiv:1810.10510v2 [cs.CV] Nov. 29, 2018 , (20 pages).

Rublee, Ethan , et al. , "ORB: An efficient alternative to SIFT or SURF" , Proceedings of the IEEE International Conference on Computer Vision. 2564-2571. 2011; 10.1109/ICCV.2011.612654 , (9 pages).

Sarlin , et al. , "SuperGlue: Learning Feature Matching with Graph Neural Networks" , Cornell University Library/Computer Science/ Computer Vision and Pattern Recognition, Nov. 26, 2019 [retrieved on Jan. 8, 2021 from the Internet< URL: https://arxiv.org/abs/1911. 11763 >, entire document.

Sattler, Torsten , et al. , "SCRAMSAC: Improving RANSAC's efficiency with a spatial consistency filter" , ICCV, 2009: 2090- 2097. , (8 pages).

Schonberger, Johannes Lutz, et al. , "Pixelwise view selection for un-structured multi-view stereo" , Computer Vision—ECCV 2016: 14th European Conference, Amsterdam, The Netherlands, Oct. 11-14, 2016, Proceedings, Part III, pp. 501-518, 2016.

Schonberger, Johannes Lutz, et al. , "Structure-from-motion revis- ited" , Proceedings of the IEEE Conference on Computer Vision and Pattern Recognition (CVPR), 2016, pp. 4104-4113 , (11 pages).

Sheng, Liu , et al. , "Time-multiplexed dual-focal plane head- mounted display with a liquid lens", Optics Letters, Optical Society of Amer i ca, US, vol. 34, No. 11, Jun. 1, 2009 (Jun. 1, 2009), XP001524475, ISSN: 0146-9592 , pp. 1642-1644.

Sinkhorn, Richard , et al. , "Concerning nonnegative matrices and doubly stochastic matrices.", Pacific Journal of Mathematics, 1967 , pp. 343-348.

Spencer, T. , et al. , "Decomposition of poly(propylene carbonate) with UV sensitive iodonium 11 salts" , Polymer Degradation and Stability; (online]. Dec. 24, 2010 (retrieved Feb. 19, 2020]. , (17 pages).

Tanriverdi, Vildan , et al. , "Interacting With Eye Movements in Virtual Environments", Department of Electrical Engineering and Computer Science, Tufts University; Proceedings of the SIGCHI conference on Human Factors in Computing Systems, Apr. 2000 , pp. 1-8.

Thomee, Bart , et al. , "YFCC100m: The new data in multimedia research" , Communications of the ACM, 59(2):64-73, 2016; arXiv:1503.01817v2 [cs.MM] Apr. 25, 2016 , (8 pages).

Torresani, Lorenzo , et al. , "Feature correspondence via graph matching: Models and global optimization" , Computer Vision— ECCV 2008, 10th European Conference on Computer Vision, Marseille, France, Oct. 12-18, 2008, Proceedings, Part II , (15 pages).

Tuytelaars, Tinne , et al. , "Wide baseline stereo matching based on local, affinely invariant regions" , BMVC, 2000 , pp. 1-14.

Ulyanov, Dmitry , et al. , "Instance normalization: The missing ingredient for fast stylization" , arXiv:1607.08022v3 [cs.CV] Nov. 6, 2017 , (6 pages).

Vaswani, Ashish , et al. , "Attention is all you need" , 31st Conference on Neural Information Processing Systems (NIPS 2017), Long Beach, CA, USA; arXiv:1706.03762v5 [cs.CL] Dec. 6, 2017 , (15 pages).

Veličković, Petar , et al. , "Graph attention networks" , ICLR, arXiv:1710.10903v3 [stat.ML] Feb. 4, 2018 , (12 pages).

Mllani, Cédric , "Optimal transport: old and new", vol. 338. Springer Science & Business Media, Jun. 2008 , pp. 1-998.

Wang, Xiaolong , et al. , "Non-local neural networks" , CVPR, arXiv:1711.07971v3 [cs.CV] Apr. 13, 2018 , (10 pages).

Wang, Yue , et al. , "Deep Closest Point: Learning representations for point cloud registration" , ICCV, arXiv:1905.03304v1 [cs.CV] May 8, 2019 , (10 pages).

Wang, Yue , et al. , "Dynamic Graph CNN for learning on point clouds" , ACM Transactions on Graphics, arXiv:1801.07829v2 [cs.CV] Jun. 11, 2019 , (13 pages).

Weissel , et al. , "Process cruise control: event-driven clock scaling for dynamic power management" , Proceedings of the 2002 inter-

(56)         References Cited

OTHER PUBLICATIONS national conference on Compilers, architecture, and synthesis for embedded systems. Oct. 11, 2002 (Oct. 11, 2002) Retrieved on May 16, 2020 (May 16, 2020) from <URL: https://dl.acm.org/doi/pdf/10.1145/581630.581668>.

Yi, Kwang Moo, et al. , "Learning to find good correspondences" , CVPR, arXiv:1711.05971v2 [cs.CV] May 21, 2018 , (13 pages).

Yi, Kwang Moo , et al. , "Lift: Learned invariant feature transform" , ECCV, arXiv:1603.09114v2 [cs.CV] Jul. 29, 2016 , (16 pages).

Zaheer, Manzil , et al. , "Deep Sets" , 31st Conference on Neural Information Processing Systems (NIPS 2017), Long Beach, CA, USA; arXiv:1703.06114v3 [cs.LG] Apr. 14, 2018 , (29 pages).

Zhang, Jiahui , et al. , "Learning two-view correspondences and geometry using order-aware network" , ICCV; aarXiv:1908.04964v1 [cs.CV] Aug. 14, 2019 , (11 pages).

Zhang, Li , et al. , "Dual graph convolutional net-work for semantic segmentation" , BMVC, 2019; arXiv:1909.06121v3 [cs.CV] Aug. 26, 2020 , (18 pages).

Zhang, Zen , et al. , "Deep Graphical Feature Learning for the Feature Matching Problem" , 2019 IEEE/CVF International Conference on Computer Vision (ICCV), IEEE, XP033723985, DOI: 10.1109/ICCV.2019.00519 [retrieved on Feb. 24, 2020] , pp. 5086-5095.

"Communication Pursuant to Article 94(3) EPC mailed on Feb. 21, 2024", European Patent Application No. 20770244.0, (8 pages).

"Communication Pursuant to Article 94(3) EPC mailed on Feb. 28, 2023", European Patent Application No. 19845418.3, (6 Pages).

"Communication Pursuant to Article 94(3) EPC mailed on Jul. 28, 2023", European Patent Application No. 19843487.0, (15 pages).

"Communication Pursuant to Article 94(3) EPC mailed on Oct. 6, 2023", European Patent Application No. 19851373.1, (6 pages).

"Extended European Search Report issued on Jan. 8, 2024", European Patent Application No. 23195266.4, (8 pages).

"Extended European Search Report issued on Jul. 20, 2022", European Patent Application No. 19885958.9, (9 pages).

"Extended European Search Report issued on Apr. 25, 2024", European Patent Application No. 23208907.8, (9 pages).

"Extended European Search Report issued on Aug. 6, 2024", European Patent Application No. 24184599.9, (14 pages).

"Extended European Search Report issued on Jul. 9, 2024", European Patent Application No. 24166847.4, (8 pages).

"Final Office Action mailed Oct. 16, 2023", U.S. Appl. No. 17/098,043, (7 pages).

"Final Office Action mailed on Dec. 1, 2023", U.S. Appl. No. 17/357,795, (18 pages).

"Final Office Action mailed on May 24, 2024", U.S. Appl. No. 18/046,739, (52 pages).

"Final Office Action mailed on Sep. 8, 2023 with English translation", Japanese Patent Application No. 2020-566620, (18 pages).

"First Examination Report Mailed on Aug. 8, 2023", Australian Patent Application No. 2018379105, (3 pages).

"First Office Action mailed Dec. 12, 2023 with English translation", Japanese Patent Application No. 2021-545712, (8 pages).

"First Office Action mailed Dec. 20, 2023 with English translation", Chinese Patent Application No. 201980050600.X, (21 pages).

"First Office Action mailed Dec. 27, 2023 with English translation", Chinese Patent Application No. 201980075942.7, (7 pages).

"First Office Action mailed Jul. 4, 2023 with English translation", Japanese Patent Application No. 2021-505669, (6 pages).

"First Office Action mailed Jun. 20, 2024 with English translation", Japanese Patent Application No. 2021-564496, (14 pages).

"First Office Action mailed Jun. 24, 2024 with English translation", Japanese Patent Application No. 2022-504602, (7 pages).

"First Office Action mailed Mar. 1, 2024 with English translation", Japanese Patent Application No. 2021-553297, (5 pages).

"First Office Action mailed Nov. 2, 2023 with English translation", Chinese Patent Application No. 201980090867.1, (16 pages).

"First Office Action mailed on Dec. 11, 2023 with translation", Chinese Patent Application No. 201980032005.3, (17 pages).

"First Office Action mailed on Dec. 25, 2023 with English translation", Chinese Patent Application No. 2019800046303.8, (13 pages).

"First Office Action mailed on Feb. 1, 2024 with English translation", Chinese Patent Application No. 202080018865.4, (9 pages).

"First Office Action mailed on Feb. 11, 2022 with English translation", Chinese Patent Application No. 201880089255.6, (17 pages).

"First Office Action mailed on Mar. 25, 2024 with English translation", Chinese Patent Application No. 202080018919.7, (31 pages).

"First Office Action mailed Sep. 29, 2023 with English translation", Japanese Patent Application No. 2023-10887, (5 pages).

"Non Final Office Action mailed on Aug. 2, 2023", U.S. Appl. No. 17/807,600, (25 pages).

"Non Final Office Action mailed on Feb. 26, 2024", U.S. Appl. No. 18/046,739, (48 pages).

"Non Final Office Action mailed on Jul. 20, 2023", U.S. Appl. No. 17/650,188, (11 pages).

"Non Final Office Action mailed on May 16, 2024", U.S. Appl. No. 18/361,546, (11 pages).

"Non Final Office Action mailed on Nov. 22, 2023", U.S. Appl. No. 17/268,376, (8 pages).

"Non Final Office Action mailed on Nov. 3, 2023", U.S. Appl. No. 17/416,248, (17 pages).

"Non Final Office Action mailed on Oct. 11, 2023", U.S. Appl. No. 17/357,795, (14 pages).

"Non Final Office Action mailed on Oct. 24, 2023", U.S. Appl. No. 17/259,020, (21 pages).

"Notice of Allowance mailed on Jul. 27, 2023 with English translation", Korean Patent Application No. 10-2020-7019685, (4 pages).

"Office Action mailed Nov. 21, 2023 with English Translation", Japanese Patent Application No. 2021-535716, (15 pages).

"Office Action mailed on Dec. 14, 2023 with English translation", Japanese Patent Application No. 2021-526564, (13 pages).

"Office Action mailed on Feb. 19, 2024 with English translation", Korean Patent Application No. 10-2020-7020552, (18 pages).

"Office Action mailed on Feb. 26, 2024 with English translation", Chinese Patent Application No. 201980069194.1, (11 pages).

"Office Action mailed on Jul. 20, 2023 with English translation", Japanese Patent Application No. 2021-505884, (6 pages).

"Office Action mailed on Mar. 6, 2024 with English translation", Chinese Patent Application No. 201980053016.X, (7 pages).

"Office Action mailed on Nov. 7, 2023 with English translation", Korean Patent Application No. 10-2023-7036734, (5 pages).

"Office Action mailed on Nov. 8, 2023 with English translation", Chinese Patent Application No. 201980060018.1, (12 pages).

"Penultimate Office Action mailed on Oct. 19, 2023 with English translation", Japanese Patent Application No. 2021-509779, (5 pages).

"Second Office Action mailed on Sep. 25, 2023 with English translation", Japanese Patent Application No. 2020-567853, (8 pages).

"Communication Pursuant to Article 94(3) EPC mailed Nov. 28, 2024", European Patent Application No. 19885958.9, (5 pages).

"Communication Pursuant to Article 94(3) EPC mailed on Feb. 7, 2025", European Patent Application No. 20154070.5, (7 pages).

"Communication Pursuant to Article 94(3) EPC mailed on Mar. 11, 2024", European Patent Application No. 20798769.4, (12 pages).

"Communication Pursuant to Article 94(3) EPC mailed on Nov. 14, 2024", European Patent Application No. 19845418.3, (4 pages).

"Communication Pursuant to Article 94(3) EPC mailed on Nov. 21, 2024", European Patent Application No. 20846338.0, (11 pages).

"Extended European Search Report issued on Dec. 2, 2024", European Patent Application No. 24167829.1, (7 pages).

"Final Office Action mailed on Aug. 15, 2024 with English translation", Japanese Patent Application No. 2021-553297, (5 pages).

"Final Office Action mailed on Dec. 13, 2024 with English translation", Japanese Patent Application No. 2021-564496, (13 pages).

"First Office Action mailed Mar. 20, 2024 with English translation", Chinese Patent Application No. 202080048293.4, (22 pages).

"First Office Action mailed Oct. 17, 2024 with English translation", Japanese Patent Application No. 2022-527990, (24 pages).

"First Office Action with English translation dated Aug. 8, 2024", Chinese Patent Application No. 202080053774.4, (23 pages).

(56)     References Cited

OTHER PUBLICATIONS

"Non Final Office Action mailed on Jan. 3, 2025", U.S. Appl. No. 18/746,709, (31 pages).
"Non Final Office Action mailed on Sep. 24, 2024", U.S. Appl. No. 18/597,716, (9 pages).
"Notice of Reasons for Rejection mailed on Dec. 4, 2024 with English tranlsation", Japanese Patent Application No. 2023-118968, (9 pages).
"Office Action mailed Feb. 20, 2025 with English translation", Japanese Patent Application No. 2024-135314, (6 pages).
"Office Action mailed on Jan. 22, 2025 with English translation", Japanese Patent Application No. 2024-63271, (8 pages).
"Office Action mailed on Nov. 7, 2024 with English translation", Korean Patent Application No. 10-2024-7032937, (7 pages).
"Office Action mailed on Oct. 4, 2024 with English translation", Japanese Patent Application No. 2022-527710, (10 pages).
"Penultimate Office Action mailed on Apr. 9, 2024—English translation", Japanese Patent Application No. 2021-535716, (3 pages).
"Penultimate Office Action mailed on Sep. 17, 2024 with English translation", Japanese Patent Application No. 2023-115047, (7 pages).
"Second Office Action with English translation mailed on Jul. 2, 2024", Chinese Patent Application No. 201980032005.3, (15 pages).
"Communication Pursuant to Article 94(3) EPC mailed on Mar. 18, 2025", European Patent Application No. 19810142.0, (8 pages).
"First Office Action mailed Apr. 22, 2025 with English translation", Chinese Patent Application No. 202211347201.X, (11 pages).
"Non Final Office Action mailed on Apr. 16, 2025", U.S. Appl. No. 18/679,328, (10 pages).
"Non Final Office Action mailed on Jun. 17, 2025", U.S. Appl. No. 18/674,016, (7 pages).
"Office Action mailed on Apr. 16, 2025 with English Translation", Japanese Patent Application No. 2024-139589, (8 pages).
"Office Action mailed on Apr. 16, 2025 with English Translation", Japanese Patent Application No. 2022-527990, (9 pages).
"Office Action mailed on Jul. 17, 2025 with English translation", Chinese Patent Application No. 202080079136.X, (42 pages).
"Office Action mailed on Mar. 17, 2025 with English Translation", Japanese Patent Application No. 2023-221068, (9 pages).
"Penultimate Office Action mailed on Aug. 13, 2025 with English translation", Japanese Patent Application No. 2024-139589, (5 pages).
"Second Office Action with English translation mailed on Mar. 25, 2025", Chinese Patent Application No. 202080053774.4, (11 pages).
"Non Final Office Action mailed on Dec. 2, 2025", U.S. Appl. No. 18/517,915, (18 pages).
"Final Office Action mailed on Dec. 17, 2025", U.S. Appl. No. 18/674,016, (8 pages).

* cited by examiner

APPARATUS FOR A NEAR-EYE DISPLAY

CROSS-REFERENCE TO RELATED APPLICATIONS

This is a continuation of U.S. patent application Ser. No. 17/713,505, filed on Apr. 5, 2022, which is a continuation of U.S. patent application Ser. No. 17/105,848 filed on Nov. 27, 2020 now U.S. Pat. No. 11,347,960, which is a continuation of U.S. patent application Ser. No. 15/552,897, filed on Aug. 23, 2017, now U.S. Pat. No. 10,878,235, which is a national stage of International Patent Application No. PCT/FI2016/050072, filed on Feb. 5, 2016, which claims priority from European Patent Application No. 15156666.8, filed on Feb. 26, 2015, each of which is incorporated herein by reference in their entirety.

TECHNOLOGICAL FIELD

Examples of the present disclosure relate to an apparatus for a near-eye display. Some examples, though without prejudice to the foregoing, relate to an apparatus for providing gaze tracking in a near-eye display.

BACKGROUND

Gaze tracking, namely the process of determining a point of gaze of a user's eye so as to determine a line of sight associated with the user's eye or to determine where the user is looking (and thus determining what the user is looking at), typically relies on capturing video images from a user's eye(s). Such video based gaze tracking typically uses infrared (IR) LEDs or infrared lasers for illuminating the eye and detecting reflections/glints of the infrared light from the eye (e.g. its cornea/surface). A determination of a user's gaze may be calculated based on the detected IR reflections and detected eye features such as detected pupil position. Conventional near-eye displays with integrated gaze tracking functionality systems are not always optimal, not least for example in view of the additional components as well as increased complexity, size and weight necessary to incorporate both gaze tracking functionality as well as display functionality in a near-eye display.

The listing or discussion of any prior-published document or any background in this specification should not necessarily be taken as an acknowledgement that the document or background is part of the state of the art or is common general knowledge. One or more aspects/examples of the present disclosure may or may not address one or more of the background issues.

BRIEF SUMMARY

An aspect of the present invention is set out in the claims.

According to at least some but not necessarily all examples of the disclosure there is provided an apparatus comprising:

a light modulator configured to receive light of a first range of wavelengths and generate an image beam therefrom, wherein the light modulator is further configured to receive light of a second range of wavelengths and generate a probe beam therefrom;

one or more light guides comprising:

one or more in-coupling diffractive element areas, and one or more out-coupling diffractive element areas;

wherein the one or more in-coupling diffractive element areas are configured to receive and in-couple the image beam and the probe beam into the one or more light guides; and wherein the one or more out-coupling diffractive element areas are configured to out-couple, from the one or more light guides:

the image beam to a user's eye for user viewing, and the probe beam to the user's eye for detection of reflection therefrom.

According to at least some but not necessarily all examples of the disclosure there is provided an apparatus comprising:

means configured to receive light of a first range of wavelengths and generate an image beam therefrom, wherein the means is further configured to receive light of a second range of wavelengths and generate a probe beam therefrom;

one or more means for guiding light comprising:

one or more in-coupling diffractive means, and one or more out-coupling diffractive means;

wherein the one or more in-coupling diffractive means are configured to receive and in-couple the image beam and the probe beam into the one or more means for guiding light; and wherein the one or more out-coupling diffractive means are configured to out-couple, from the one or more means for guiding light:

the image beam to a user's eye for user viewing, and the probe beam to the user's eye for detection of reflection therefrom.

According to at least some but not necessarily all examples of the disclosure there is provided an apparatus comprising:

means configured to generate an image beam of light at a first range of wavelengths, wherein the means is further configured to generate a probe beam of light of a second range of wavelengths;

one or more means for guiding light comprising:

one or more in-coupling diffractive means, and one or more out-coupling diffractive means;

wherein the one or more in-coupling diffractive means are configured to receive and in-couple the image beam and the probe beam into the one or more means for guiding light; and wherein the one or more out-coupling diffractive means are configured to out-couple, from the one or more means for guiding light:

the image beam to a user's eye for user viewing, and the probe beam to the user's eye for detection of reflection therefrom.

Certain examples of the apparatus may be provided as a module for a device or as a device itself. The device may be configured for at least one of: portable use, wearable use, head mountable use. Certain examples of the apparatus are configured for use with a Near Eye Display (NED) for providing both display and gaze tracking functionality.

The examples of the present disclosure and the accompanying claims may be suitably combined in any manner apparent to one of ordinary skill in the art.

BRIEF DESCRIPTION OF THE DRAWINGS

For a better understanding of various examples of the present disclosure that are useful for understanding the detailed description and certain embodiments of the invention, reference will now be made by way of example only to the accompanying drawings in which.

DETAILED DESCRIPTION

Figure 1:
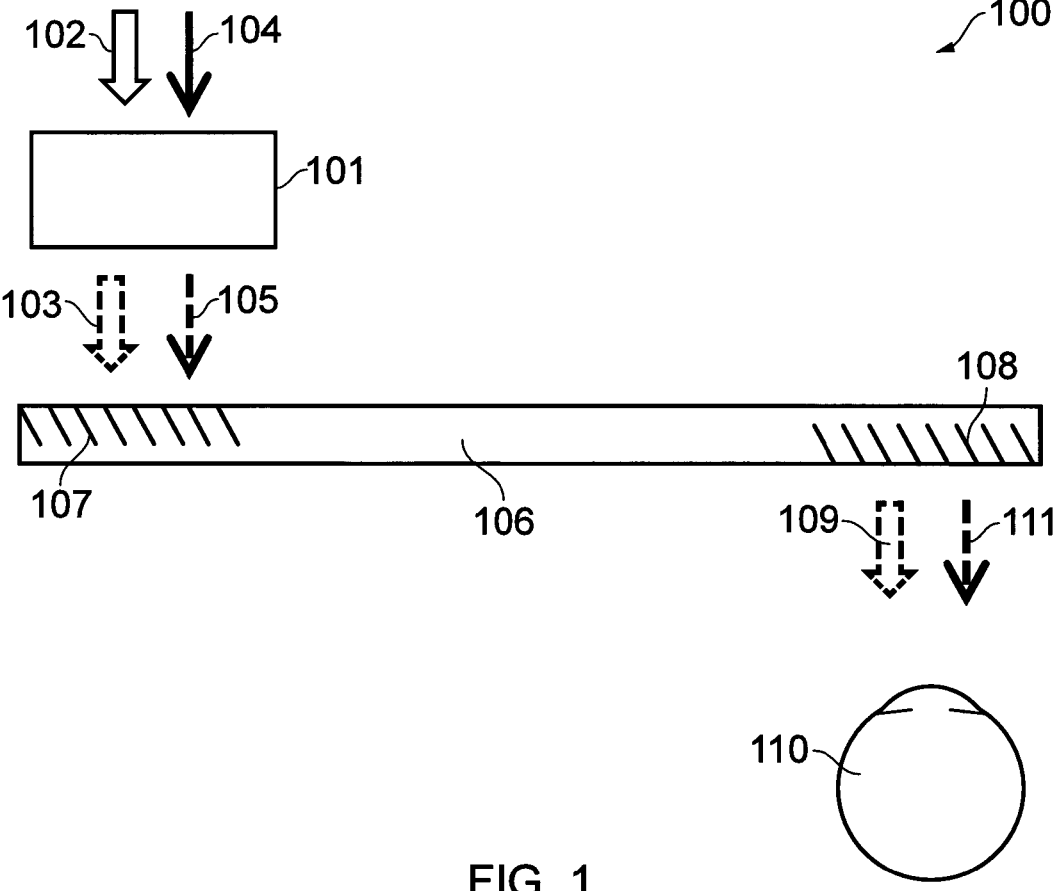
FIG. 1 schematically illustrates an example of an apparatus according to the present disclosure.

Examples of apparatuses according to the present disclosure will now be described with reference to the Figures. Similar reference numerals are used in the Figures to designate similar features. For clarity, all reference numerals are not necessarily displayed in all figures.

FIG. 1 schematically illustrates a block diagram of an apparatus 100 according to an example of the present disclosure. FIG. 1 focuses on the functional components necessary for describing the operation of the apparatus.

The apparatus 100 comprises a light modulator 101 configured to receive light of a first range of wavelengths 102, and generate an image beam 103 therefrom. The light modulator 101 is further configured so as to receive light of a second range of wavelengths 104 and generate a probe beam 105 therefrom.

The apparatus 100 further comprises one or more light guides 106 comprising one or more in-coupling diffractive element areas 107, and one or more out-coupling diffractive element areas 108. The one or more in-coupling diffractive element areas 107 are configured to receive and in-couple the image beam 103 and the probe beam 105 into the one or more light guides 106. The one or more out-coupling diffractive element areas 108 are configured to out-couple, from the one or more light guides 106:

the image beam 109 to a user's eye 110 for user viewing, and the probe beam 111 to the user's eye 110 for detection of reflection therefrom.

Figure 5A:
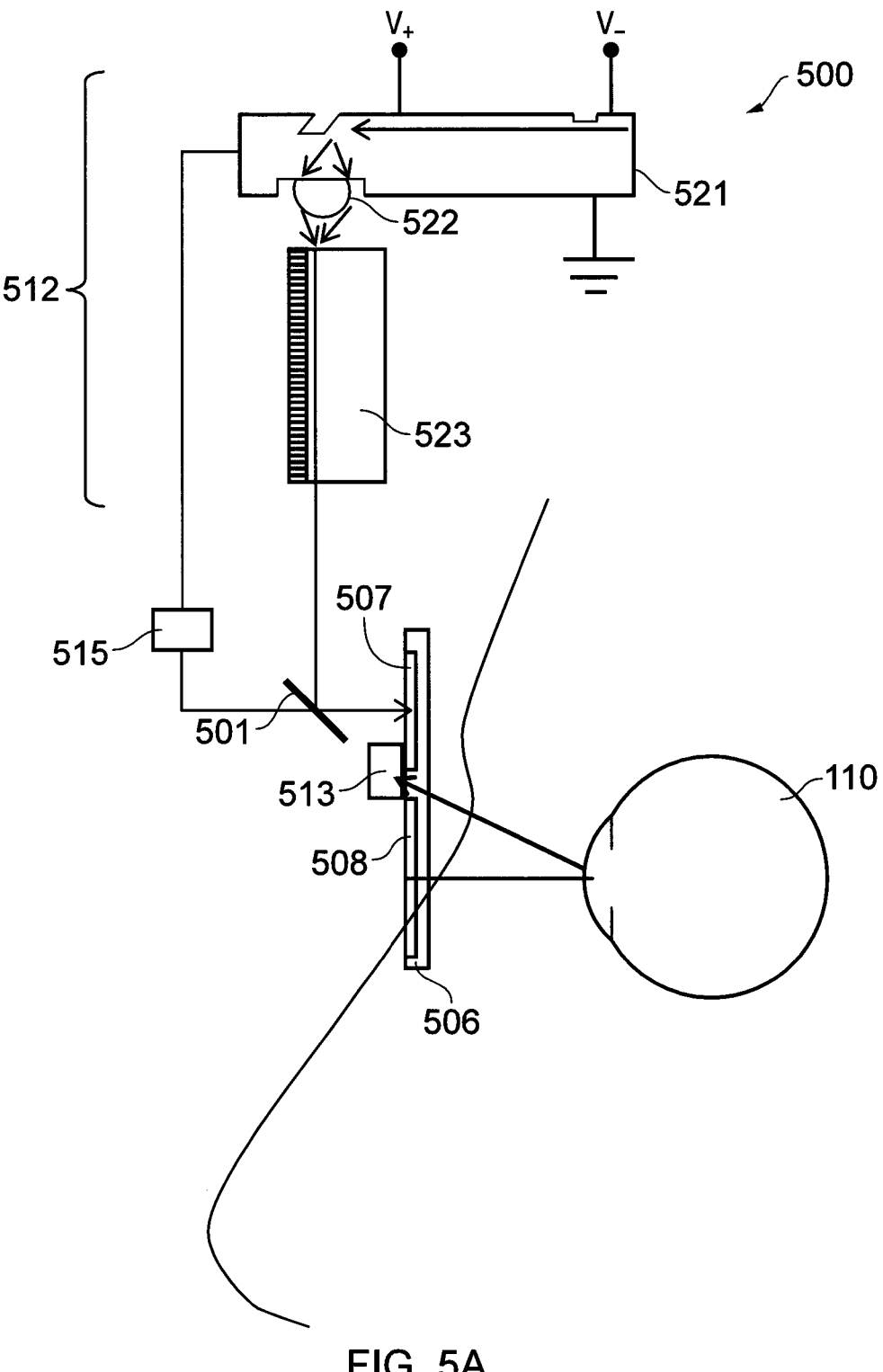
FIGS. 5A and 5B schematically illustrate examples of light modulators suitable for use with examples of the present disclosure.
Figure 5B:
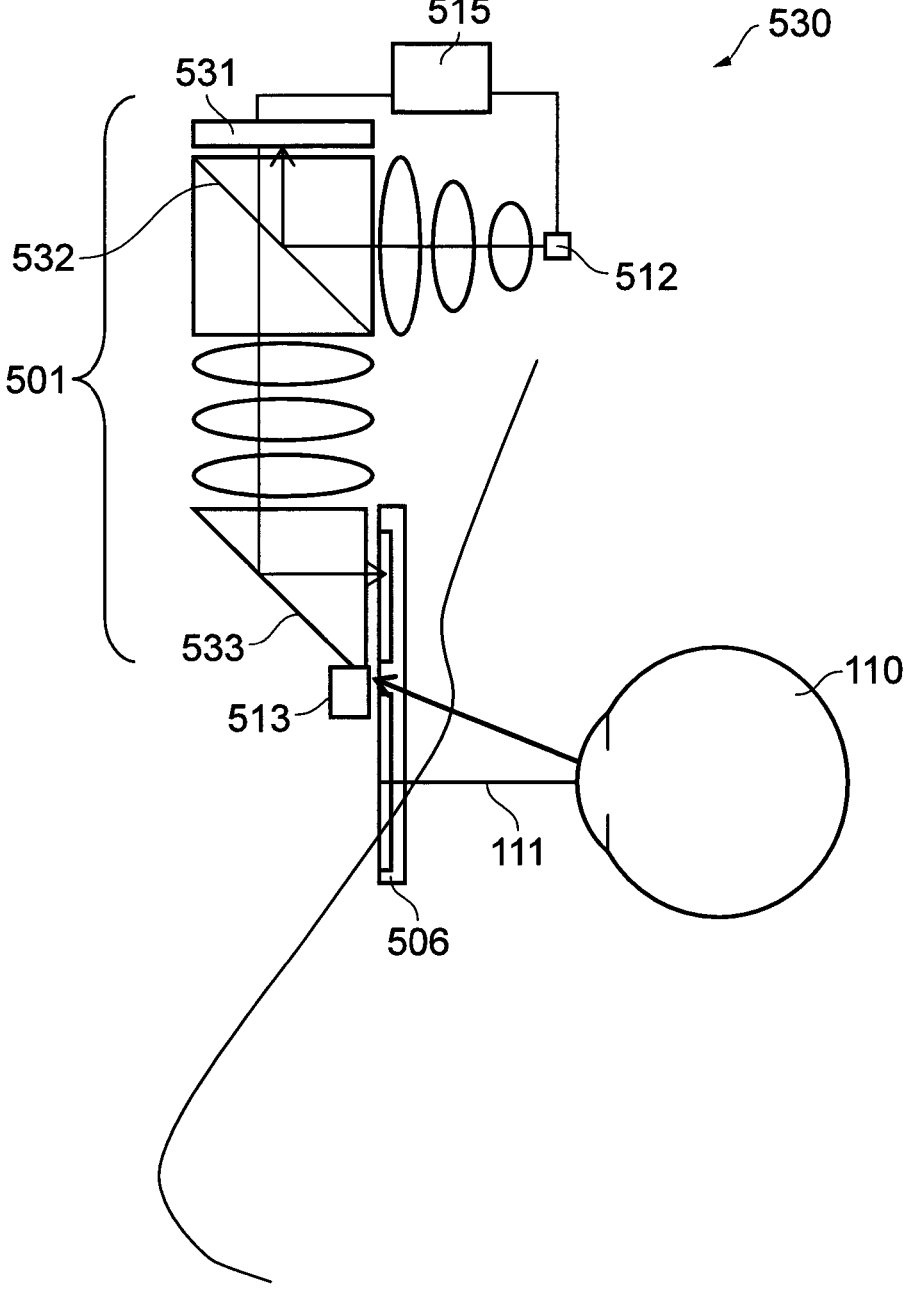

Each of the components described above may be one or more of any element, device, mechanism or means configured to perform the corresponding functions of the respective components as described in greater detail below. The component blocks of FIG. 1 are functional and the functions described may or may not be performed by a single physical entity for example the light modulator 101 may correspond to an assembly/arrangement of components, not least for example as shown in FIG. 5A or FIG. 5B. Accordingly, the blocks support: combinations of means for performing the specified functions.

The light modulator 101 may comprise a light modulating/modifying means configured to modulate/modify the incident light 102, 104 of first and second ranges of wavelengths so as to impart an image or pattern thereon and generate one or more collimated beams 103, 105 comprising a variable image or pattern. The light modulator 101 may comprise one or more of: an optical engine, a light engine, a micro display, optics (e.g. enlarging optics and collimating optics), a projector, a digital light processing (DLP) system, a liquid crystal on silicone (LCoS), a retinal scan display, a laser scanning system, a microelectromechanical (MEM) system (e.g. for providing scanning/raster scanning). The light modulator 101, in certain examples, may be: a reflective based display, a transmissive based display or an emissive based display.

In some examples, instead of receiving light of a first and a second range of wavelengths and generating an image beam and probe beam therefrom, the light modulator may be configured to be able to generate for itself an image beam of light of a first range of wavelengths and a probe beam of light of a second range of wavelengths. For example the light modulator may comprise one or more display elements which itself creates a pixelated image/probe pattern that is then projected through an optical setup, e.g. an OLED display or an LED array display, for in-coupling to the one or more light guides.

The image beam 103 may comprise a collimated beam of light that may be expanded and guided to user's eye 110 for viewing and perceiving the image which is imparted to the light 102 that forms the image beam 103 by the light modulator 101. Where the light 102 of the first range of wavelengths comprises one or more colour channels of visible light, e.g. one or more of red (R), green (G) and blue (B), the image beam 103 may correspondingly comprise light within the visible range of the electromagnetic spectrum, e.g. one or more of R, G and B. In certain examples, one or more image beams may be generated corresponding to the image in differing colour channels, e.g. one or more of R, G and B, from light received in the respective colour channels.

The probe beam 105 may comprise a collimated beam of light that may be expanded and guided to user's eye 110 for reflection therefrom. In certain examples (see FIG. 2), such reflection is detected and used in part to determine a gaze or direction of view of the eye 110. The light modulator 101 may impart a variable pattern, image, shape or size to light 104 that forms the probe beam 105. Where the light of the second range of wavelengths comprises infrared light the probe beam may correspondingly comprise light within the infrared part of the electromagnetic spectrum.

The one or more light guides 106 may comprise light guiding means comprising one or more means for diffracting beams into and out of the light guide, for example a diffractive optical element. The light guides may, for example, be a one or more substantially planar substrates comprising one or more areas or diffractive elements/gratings/grooves that are disposed on lower or upper surfaces of the substrate or even located internally of the substrate. The light guide may be an exit pupil expander configured to expand an incident beam of light 103, 105 in one or more directions. The light guides may be transparent and the apparatus may be configured such that the user can see the real world though the apparatus/light guides whilst also seeing a virtual image/world via the apparatus/light guides.

Certain examples of the apparatus: may reduce the complexity of a combined display and gaze tracking device, may provide improved integration and require fewer components, and may thus also reduce the weight and size of the apparatus by enabling the sharing/reutilisation of various components. This may enable the provision of a miniaturised and efficient apparatus for integrated NED and Gaze tracking. For example, the light modulator 101 which generates the image beam 103 is also used to generate the probe beam 105. In other examples, a light source for emitting the light for the image beam 103 is also used to generate the light for the probe beam 105.

The use of the light modulator 101 to generate the probe beam 105 may enable a pattern, shape or size of the probe beam to be dynamically varied. Such control of the probe beam may enable the creation of complex variable shapes, sizes, patterns/images of the probe beam. Moreover, the probe beam could be dynamically adjusted during use so as to achieve optimal detection and measurement results thereby enabling more robust gaze tracking as well as simpler gaze tracking calibration.

Furthermore, certain examples (e.g. FIG. 1) provide the ability to share/utilise one or more of in-coupling diffractive elements 107 and/or one or more of the out-coupling diffractive elements 108 to in-couple and/or out-couple both the image beam 103 and the probe beam 105 and may thereby reduce the number of optical components and the complexity of the arrangements of such components that may otherwise have been required to direct each of the image beam and probe beam separately and independently.

Furthermore, certain examples (see e.g. FIG. 5A) may enable the use of a combined light source 512 which simultaneously generates both the light 102 for the image beam 103 as well as light 104 for the probe beam 105 and may thereby reduce the number of components (and thus the weight, size and complexity) of the apparatus.

In the example of FIG. 1, the light guide 106 comprises a substrate of an optical material having first and second opposing surfaces. The substrate comprises an area of in-coupling diffractive elements 107 and an area of out-coupling diffractive elements 108 which may be laterally spaced apart from one another on the planar substrate for example at either end of the substrate. The in-coupling diffractive element area is configured to receive one or more input optical beams, i.e. either the image beam 103 ("image display beam") or the probe beam 105 ("gaze tracking probe beam"), and diffract the input optical beam substantially within the first and second surfaces to provide a diffracted optical beam within the substrate which is coupled via total internal reflection to the out-coupling diffractive element area 108. The out-coupling diffractive element area is configured to further diffract the diffracted optical beam out of the substrate to provide an output optical beam, namely an output of the image display beam 109 or the output gaze tracking probe beam 111.

Figure 3:
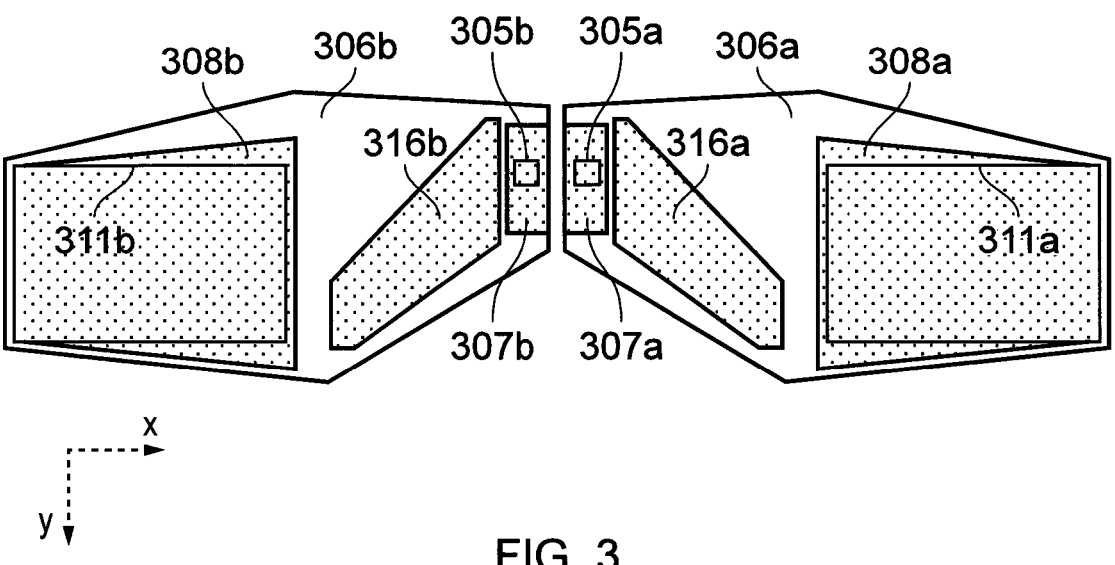
FIG. 3 schematically illustrates an example of diffractive light guides suitable for use with examples of the present disclosure.

The out-coupling diffractive element 108 may be configured so as to not only just output the diffracted optical beam from the substrate but also to expand the diffracted optical beam in one direction. Further diffractive elements may be provided (for example 316a as shown in FIG. 3) for expanding the diffracted optical beam in another direction so as to provide an output beam 109, 111 that can be expanded beam in two directions.

In certain examples, the in-coupling and out-coupling elements may be based on other optical methods than diffraction gratings and groves, for example volume holograms or gratings, or semi-transparent mirror structures.

The apparatus of FIG. 1 shows a schematic illustration of a monocular apparatus. However, it is to be appreciated that the apparatus could be configured in a binocular form. Such a binocular form could correspond to providing two apparatuses 100 one for each of the user's eyes. For example, providing apparatus 100 shown in FIG. 1 for a user's right eye and a mirror image version of the apparatus 100 for the user's left eye (similar to that of FIG. 2). As an alternative to using two such laterally adjacent light guides, a single light guide could be provided having an in-coupling diffractive element area between two out-coupling diffractive element areas located at either end of the light guide wherein the in-coupling diffractive element area is configured to provide two diffracted input optical beams, one coupled to one of the out-coupling diffractive element areas, for example at a left hand end of the light guide, and the other diffracted input optical beam coupled to the other of the out-coupling diffractive element areas at the other end, e.g. a right hand end of the light guide.

FIG. 1 shows a single diffractive light guide 106 provided with one in-coupling diffractive element area 107 which is configured to diffract light at the first range of wavelengths (e.g. in the visible part of the electromagnetic spectrum) as well as light at the second range of wavelengths (e.g. the IR part of the electromagnetic spectrum). Thus, the diffractive element area 107 may be configured to in-couple both the image display beam as well as the gaze tracking probe beam, i.e. the diffractive element may be configured so as to diffract (or at least have an acceptable efficiency for diffracting) each of infrared, red, green and blue colour channels regions of the electromagnetic spectrum or to diffract a portion of a colour channel. It should be appreciated that other colour channels/apportionment of the visible spectrum may also be envisaged. Likewise, the single out-coupling diffractive element 108 may be similarly configured to diffract and out-couple a corresponding wide range of wavelengths.

As an alternative to using a single in-coupling diffractive element area for in-coupling a wide range of wavelengths of input beams 103, 105, a plurality of in-coupling diffractive element areas could be provided on a light guide, each area spatially distinct from another and each being configured and optimised to diffract a particular/narrower range of wavelengths, for example one or more colour channels, infrared, red, green or blue, to provide one or more diffractive optical beams of such wavelengths of light within the substrate for out-coupling from the substrate by one or more out-coupling diffractive element areas.

Likewise, a plurality of out-coupling diffractive elements could be provided on the light guide each configured and optimised to diffract a particular narrow range of wavelengths of light and out-couple them from the light guide.

Yet further alternatively, instead of having a single light guide (with one or more in-coupling diffractive element areas and one or more out-coupling diffractive element areas) a plurality of light guides may be provided, e.g. vertically aligned and stacked on top of each other. Each of the stacked light guides could be provided with one or more in/out-coupling diffractive element areas configured and optimised to in-couple and out-couple one or more particular colour channels. Thus, it is to be appreciated that a variety of possible combinations of: numbers of in- and out-coupling diffractive element areas per light guide, as well as number of stacked light guides are envisaged.

Figure 2:
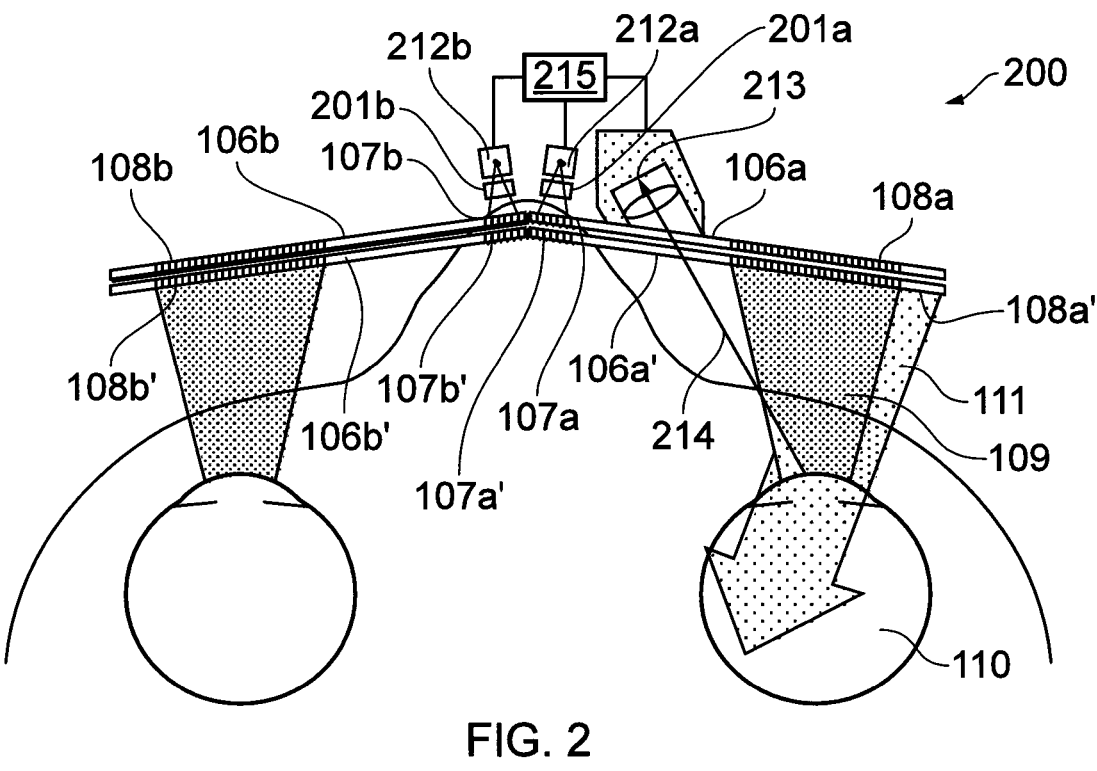
FIG. 2 schematically illustrates a further example of an apparatus according to the present disclosure.

FIG. 2 shows an apparatus 200 in a binocular form comprising a right hand side set of stacked light guides 106a and 106a' along with a left hand side set of stacked light guides 106b and 106b'. For the sake of simplicity, the below discussion focuses just on the right hand side components of the apparatus. It is to be appreciated that similar components may be provided on the left hand side of the apparatus (with equivalent reference numerals but designated with a "b" instead of "a").

Of the two stacked light guides 106a and 106a', one is configured and optimised to in-couple, expand and out-couple visible light for example in the green and blue parts of the spectrum, whereas the other light guide is configured and optimised to in-couple, expand and out-couple infrared light and red light.

It is to be appreciated that other permutations may readily be envisaged, not least for example a plurality of stacked light guides each optimised for one of: blue, green, red and infrared respectively, or, similarly to FIG. 1, a single light guide may be provided for in- and out-coupling all of IR, R, G and B wavelengths of light beams. Also, one light guide optimised for RGB could be provided with another optimised for IR. Such an IR optimised light guide could be made to be thinner than an RGB light guide. It could further be configured for other integrated uses, such as: being used as a protective element, or a capacitive measurement surface for face/eye movement detection as well as an LC shutter and hot mirror as discussed in further details below.

A single light source 212a emits light 102, 104 for both the image display beam 103 (i.e. visible light) as well as light for the gaze tracking probe beam 105, (i.e. infrared light). Such a light source generating simultaneously both visible light and infrared light may correspond to a laser crystal on silicone based light source as discussed further with respect to FIG. 5A. Alternatively, instead of having a light source that generates simultaneously both the visible and infrared light, separate light sources may be provided which generate independently visible light and infrared, for example separate light sources configured to emit each of visible light and infrared light, not least for example separate red, green, blue and infrared LEDs positioned adjacent to one another which can be separately and independently controlled/switched on such that only visible light is emitted and received by the light modulator when generating the display imaging and likewise only infrared light is emitted and received at the light modulator when generating the gaze tracking probe beam.

The light source 212a generates the light of the first range of wavelengths 102 and also generates the light of the second range of wavelengths 104, each of which are incident to a light modulator 201a which generates an image display beam 103 and a gaze tracking probe beam 105 from such incident light respectively. Additional optics, e.g. lenses, mirrors or MEM system may be provided as well as other mechanisms for focusing, collimating the source of light into beams of light that may further be scanned/rastered into the in-coupling diffractive element.

The image display beam from the light modulator 201a is incident to a first in-coupling diffractive element area 107a and in-coupled into the first light guide 106a and then out-coupled via out-coupling diffractive element 108a (propagating through the underlying light guide 106a') so as to be directed towards a user's eye 110. The first light guide may be configured and optimised so as to in-couple, expand and out-couple light of the image display beam in green and blue parts of the visible spectrum. The further light guide 106a' may be provided with an in-coupling diffractive element area 107a' and an out-coupling diffractive element area 108a' configured and optimised to in-couple, expand and diffract out visible light of the image display beam in the red part of the spectrum. The second light guide 106a' may further be configured to in-couple, expand and out-couple infrared light to provide an output gaze tracking probe beam 111 which is incident to the user's eye to be reflected therefrom.

A detector 213, such as an IR detector/sensor or camera, may be provided to detect reflections 214 of the gaze tracking probe beam from the user's eye, i.e. images/video of the user's eye in IR. The detection and measurement of such reflections 214 of the infrared gaze tracking probe beam may be used in part by a controller 215 to calculate and determine a user's gaze.

In some examples, other features of the eye are also measured and captured, for example related to a location of the user's eye pupil. In some examples, the IR detector/eye camera is used to capture and measure not only the reference reflections/glints 214 but is also used to capture and measure a location of the eye pupil. A determination may be made of the detected location of the reference reflection 214 relative to the detected location of the pupil. Differences of the relative movement between the pupil and the reference reflections 214 can be used for detecting changes in the gaze direction.

The determination of the gaze may also be dependent on the generated gaze tracking probe beam, i.e. taking into account one or more characteristics of the generated infrared probe beam outputted such as its initial shape, size and intensity prior to being reflected from the user's eye as compared to the shape, size and intensity of the detected reflected gaze tracking probe beam.

Implementation of the controller 215 can be in hardware alone (e.g. circuitry such as processing circuitry comprising one or more processors and memory circuitry comprising one or more memory elements), have certain aspects in software including firmware alone or can be a combination of hardware and software (including firmware).

The controller 215 may be used to control one or more of the light source 212a and the light modulator 201a so as to control each of the image display beam and the gaze tracking probe beam. The generated gaze tracking probe beam may be modified, e.g. its size or shape or intensity, depended upon the detected reflected gaze tracking probe beam. Such feedback from the detection of the reflected gaze tracking probe beam can assist in the calibration of the apparatus and enable for the gaze tracking probe beam's pattern, shape or size to be optimised for the prevailing circumstances of use.

Whilst FIG. 2 shows a single detector 213 for detecting the gaze of one eye, i.e. the user's right eye, the arrangement could be modified to, alternatively or additionally, determine the gaze of the user's other eye. Whilst FIG. 2 shows a single detector 213 for detecting the gaze of one eye, i.e. the user's right eye, the arrangement could be modified to determine the gaze of the eye using two or more detectors. Whilst FIG. 2 shows two light sources 212a and 212b, and two modulators 201a and 201b, a single light source and/or a single light modulator could be provided for generate image display and probe beams that are incident to each of the two in-coupling diffractive element areas 107a and 107b.

In the apparatus of FIG. 2, where a combined visible and infrared light source is used, i.e. that simultaneously generates both visible and infrared light (as opposed to separately and independently generating visible and IR light such that the emission of visible and IR light can be separately and independently controlled), the apparatus may further comprise a selectively controllable filter to selectively filter out one of: the visible light (or a sub colour channel thereof) or the infrared light.

In some examples, e.g. where the IR optimised light guide is below (and disposed closer to the eye than) the RGB optimised light guide, a passive IR pass filter could be placed between the in-coupling area of the RGB optimised light guide and the in-coupling area of the IR optimised light guide, e.g. so as to reduce in-coupling of RGB light to the IR light guide. Alternatively, in other examples, e.g. where the RGB optimised light guide is below (and placed closer to the eye than) the IR optimised light guide, an IR blocking filter could be placed between the respective in-coupling areas, e.g. so as to reduce in-coupling of IR light to the RBG light guide.

In some examples a Liquid Crystal (LC) shutter could be placed between the light guides and the outside environment/world/reality. For example the LC shutter could form part of a selectively transparent part of the external housing of the apparatus which is configured to selectively enable a real world view though the apparatus. Adjusting the shutter's transmissivity would control how much ambient light gets to the eye through the shutter and through the transparent light guides. The LC shutter could, in some examples, be integrated into an IR optimised light guide, in which case such a light guide may be placed between the RGB optimised light guide(s) and the outside environment/world/reality so that it would not block the RGB light from the light guide reaching the eye.

In some examples, the light guide 106a' which in-couples, expands and out-couples the infrared gaze tracking probe beam may be configured so as to selectively filter the transmission of infrared light therethrough. The light guide 106a' may be configured to act as a liquid crystal shutter that can selectively block the transmission of infrared light therethrough whilst still permitting the transmission of visible light therethrough.

When an image display beam is being generated and outputted, a selectively controllable filter may be used to block infrared light such that only visible light is incident to the user's eye during periods of outputting the image display beam output for user viewing. Likewise, in other examples, visible light may be selectively filtered/blocked/switched off such that only infrared gaze tracking light probe beam may be generated and incident to the user's eye when outputting an infrared gaze tracking probe beam.

FIG. 3 schematically illustrates an example of light guides 306a and 306b suitable for use with examples of the present disclosure. For example, the light guides 306a and 306b may be configured for use as light guides 106a and 106b, or 106a' and 106b' of FIG. 2.

The light guide 306a comprises in-coupling diffractive area 307a which in-couples an input beam 305a to the substrate, which beam is then expanded via diffractive element area 316a in a y direction and then expanded in an x direction and out-coupled out of the light guide via an out-coupling diffractive element 308a so as to produce output beam 311a. The input optical beam 305a may correspond to an image display beam (or a component of the image display beam such as a red, green or blue component thereof) or an infrared gaze tracking probe beam.

Figure 4:
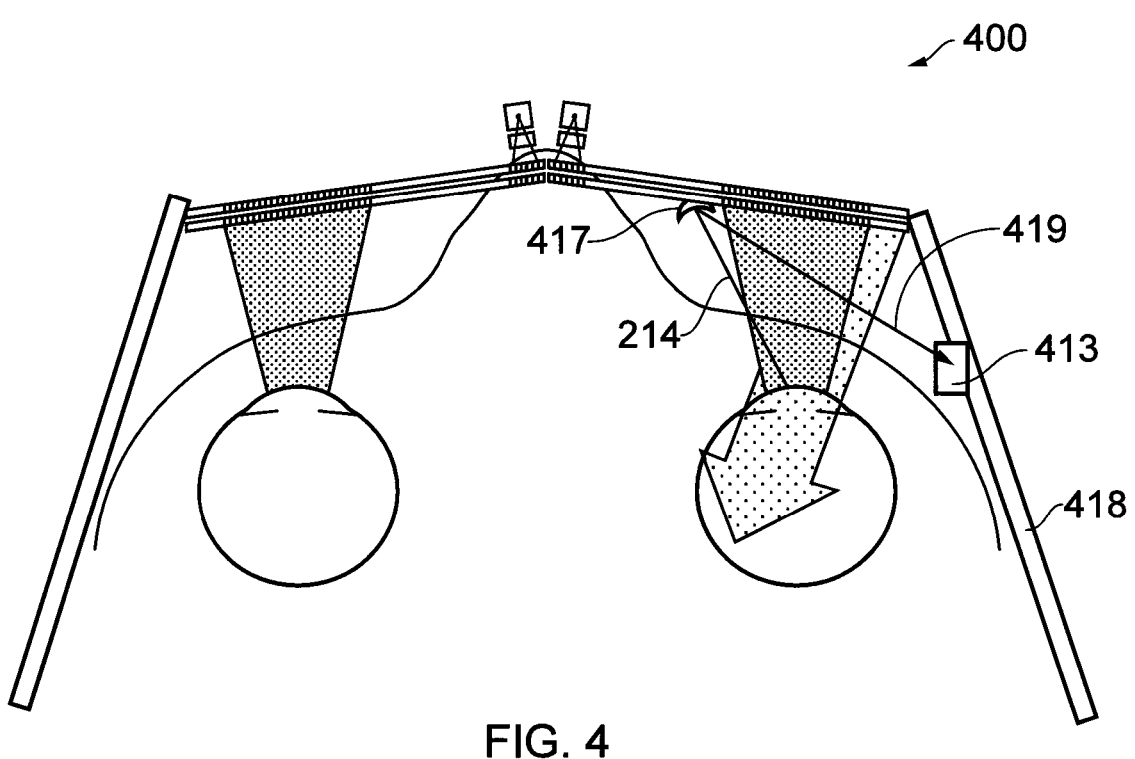
FIG. 4 schematically illustrates a yet further example of an apparatus according to the present disclosure.

In the apparatus of FIG. 2, the reflected gaze tracking probe beam 214 needs to propagate through each of the stacked light guides 106a' and 106a to reach the detector for detection. FIG. 4 schematically shows an apparatus 400 that avoids such issues.

FIG. 4 schematically shows an apparatus in the form of glasses/goggles with support members/arms 418 for holding the apparatus in place on a user's head. In this example, the detector 413 is not disposed on the light guides. Instead, a reflector element 417, such as a mirror or hot mirror configured to reflect infrared light, is provided e.g. on in the light guide, namely an inner/lower surface of the lower light guide. It is to be appreciated that the reflector element could be located almost anywhere in front of the eye, even on an opposite side of the light guide stack.

The reflector is configured to further reflect 419 the reflected gaze tracking beam to a detector 413, thereby providing increased flexibility as to the location of the detector. In this example, the detector is disposed on a part of a housing of the apparatus such as support arm 418. The reflector 417 may be further configured so as to provide optical power so as to focus the reflected infrared gaze tracking probe beam 214 towards the detector 413.

FIG. 5A schematically illustrates an example of an apparatus 500 comprising a combined/highly integrated visible and infrared light source 512 which may be used as a laser projector engine. A laser diode 521 generates infrared light which is focused by lens 522 into a non-linear crystal 523, such as periodically poled lithium niobate (PPLN), comprising a surface bragg grating whereby the infrared light is converted into red, green and blue visible wavelengths. However, some infrared light will pass through the non-linear crystal without undergoing such conversion. A conventional laser projection engine would typically block such non-converted infrared light deeming it to be an undesired noise signal. However, such non-converted infrared light may advantageously be used in examples of the present application as a source of infrared illumination. Thus, the light source 512 provides the simultaneous generation of both visible light as well as infrared light that can be incident to a light modulator 501, under control of a controller 515, so as to sequentially generate an image display beam and a gaze tracking probe beam from the incident visible and infrared beams respectively. A selectively controllable filter or shutter may be used to selectively filter/block IR light when the image display beam is being generated and likewise selectively filter/block visible light when the gaze tracking probe beam is being generated.

The light modulator 501 comprises a two axis scanning mirror which can be used to impart an image to the visible light from the light source to generate the image display beam. Also, the light modulator can be used to impart a pattern on the infrared light from the light source to generate the gaze tracking probe beam.

FIG. 5B schematically illustrates an apparatus 530 with an alternative light source 512 and an alternative light modulator 501. The light source 512 is configured to independently and separately generate visible light (and/or sub component colour channels thereof) and infrared light. The light source 512 may corresponds to one or more separate light sources, e.g. LEDs, such as: red, green, blue and infrared LEDs which are independently operable under control of a controller 515. Light from the LEDs is directed to a reflective microdisplay 531 via beam splitter 532. The modulated/modified light reflected from the microdisplay is then guided to a prism 533 and reflected therefrom to an in-coupling diffractive element area 507 of a light guide 506 to be out-coupled to a user's eye 110 via out-coupling diffractive element area 508. A detector 513 is provided that is configured to detect the out-coupled light which is reflected from the user's eye.

The apparatuses as variously described above may be provided in a module. As used here 'module' refers to a unit or apparatus that excludes certain parts/components that would be added by an end manufacturer or a user.

In certain examples, the apparatus may be provided as a device, wherein a device is configured for at least one of portable use, wearable use and head mountable use. The device may also be configured to provide functionality in addition to display and gaze tracking. For example, the device may additionally be configured to provide one or more of: audio/text/video communication functions (e.g. tele-communication, video-communication, and/or text transmission (Short Message Service (SMS)/Multimedia Message Service (MMS)/emailing) functions), interactive/non-interactive viewing functions (e.g. web-browsing, navigation, TV/program viewing functions), music recording/playing functions (e.g. Moving Picture Experts Group-1 Audio Layer 3 (MP3) or other format and/or (frequency modulation/amplitude modulation) radio broadcast recording/playing), downloading/sending of data functions, image capture function (e.g. using a (e.g. in-built) digital camera), and gaming functions.

The apparatus may be a part of a NED device, for example, glasses or goggles. It should be understood, however, that glasses or goggles are merely illustrative of an NED device that would benefit from examples of implementations of the present disclosure and, therefore, should not be taken to limit the scope of the present disclosure to the same. For example the apparatus may take other forms such as a visor or helmet or may be implemented in other electronic devices not least hand devices, or portable devices.

Although examples of the apparatus have been described above in terms of comprising various components, it should be understood that the components may be embodied as or otherwise controlled by a corresponding processing element, processor or circuitry of the apparatus.

As used in this application, the term 'circuitry' refers to all of the following:

(a) hardware-only circuit implementations (such as implementations in only analogue and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware.

Features described in the preceding description may be used in combinations other than the combinations explicitly described.

Although functions have been described with reference to certain features, those functions may be performable by other features whether described or not. Although features have been described with reference to certain examples, those features may also be present in other examples whether described or not. Although various examples of the present disclosure have been described in the preceding paragraphs, it should be appreciated that modifications to the examples given can be made without departing from the scope of the invention as set out in the claims.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, wording such as 'couple', 'connect' and 'communication' and their derivatives mean operationally coupled/connected/in communication. It should be appreciated that any number or combination of intervening components can exist (including no intervening components).

In this description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some or all other examples. Thus 'example', 'for example' or 'may' refers to a particular instance in a class of examples. A property of the instance can be a property of only that instance or a property of the class or a property of a sub-class of the class that includes some but not all of the instances in the class.

In this description, references to "a/an/the" [feature, element, component, means . . . ] are to be interpreted as "at least one" [feature, element, component, means . . . ] unless explicitly stated otherwise.

The above description describes some examples of the present disclosure however those of ordinary skill in the art will be aware of possible alternative structures and method features which offer equivalent functionality to the specific examples of such structures and features described herein above and which for the sake of brevity and clarity have been omitted from the above description. Nonetheless, the above description should be read as implicitly including reference to such alternative structures and method features which provide equivalent functionality unless such alternative structures or method features are explicitly excluded in the above description of the examples of the present disclosure.

Whilst endeavouring in the foregoing specification to draw attention to those features of examples of the present disclosure believed to be of particular importance it should be understood that the applicant claims protection in respect of any patentable feature or combination of features hereinbefore referred to and/or shown in the drawings whether or not particular emphasis has been placed thereon.

I claim:

1. An apparatus comprising:

a light source configured to generate simultaneously light of a first range of visible wavelengths, and light of a second range of visible wavelengths in an image beam;

first and second light guides, each comprising:

an in-coupling diffractive element area configured to receive and in-couple the image beam into the respective light guide;

a diffractive element area having a first repeated diffraction spacing; and an out-coupling diffractive optical element positioned to out-couple, from the first and second light guides respectively, the image beam to a user's eye for user viewing, the out-coupling diffractive optical element having a second repeated diffraction spacing that is different from the first repeated diffraction spacing, wherein the first and second light guides respectively transmit the light of the first range of visible wavelengths and the light of the second range of visible wavelengths, wherein the diffractive element of the first light guide is superposed on and aligned with the diffractive element of the second light guide; and the second out-coupling diffractive optical element of the first light guide is superposed on and aligned with the second out-coupling diffractive optical element of the second light guide; and a third light guide, comprising:

an in-coupling diffractive element area configured to receive and in-couple the probe beam into the respective light guide;

a diffractive element area having a first repeated diffraction spacing; and an out-coupling diffractive optical element positioned to out-couple, from the third light guide, the probe beam to the user's eye for detection of reflection therefrom, the out-coupling diffractive optical element having a second repeated diffraction spacing that is different from the first repeated diffraction spacing.

2. The apparatus of claim 1, further comprising a detector configured to detect reflections of the probe beam.

3. The apparatus of claim 2, further comprising a controller to modify the probe beam dependent upon the detection of the reflected probe beam.

4. The apparatus of claim 2, further comprising a reflector configured to further reflect the reflected probe beam to the detector.

5. The apparatus of claim 2, further comprising a controller to determine a user's gaze based on the detected reflected probe beam.

6. The apparatus of claim 1, further comprising a selectively controllable filter to selectively filter one of, the light of the first range of wavelengths and the light of the second range of wavelengths.

7. The apparatus of claim 1, further comprising a light source configured to generate sequentially the light of the first range of wavelengths and the light of the second range of wavelengths.

8. The apparatus of claim 1, wherein the one or more light guides is configured as an exit pupil expander.

9. The apparatus of claim 1, wherein the apparatus is configured for use as a near eye display and a gaze tracker.

10. The apparatus of claim 1, wherein the apparatus is configured for use as a near eye display and a gaze tracker.

* * * * *